United States Patent
Lähteenkorva et al.

(10) Patent No.: US 12,383,660 B2
(45) Date of Patent: Aug. 12, 2025

(54) COMPOSITE MATERIAL, IMPLANT COMPRISING THEREOF, USE OF THE COMPOSITE MATERIAL AND METHODS FOR PREPARING THE COMPOSITE MATERIAL AND A MEDICAL DEVICE

(71) Applicant: BIORETEC OY, Tampere (FI)

(72) Inventors: Kimmo Lähteenkorva, Tampere (FI); Tomi Numminen, Turku (FI)

(73) Assignee: BIORETEC OY, Tampere (FI)

( * ) Notice: Subject to any disclaimer, the term of this patent is extended or adjusted under 35 U.S.C. 154(b) by 658 days.

(21) Appl. No.: 17/636,404

(22) PCT Filed: Aug. 21, 2020

(86) PCT No.: PCT/EP2020/073515
§ 371 (c)(1),
(2) Date: Feb. 18, 2022

(87) PCT Pub. No.: WO2021/032882
PCT Pub. Date: Feb. 25, 2021

(65) Prior Publication Data
US 2022/0296789 A1    Sep. 22, 2022

(30) Foreign Application Priority Data
Aug. 21, 2019 (EP) .................................... 19397525

(51) Int. Cl.
*A61L 31/14* (2006.01)
*A61L 27/04* (2006.01)
(Continued)

(52) U.S. Cl.
CPC .......... *A61L 31/148* (2013.01); *A61L 27/047* (2013.01); *A61L 27/10* (2013.01); *A61L 27/34* (2013.01);
(Continued)

(58) Field of Classification Search
CPC ...... A61L 31/148; A61L 27/047; A61L 27/10; A61L 27/34; A61L 31/022; A61L 31/026
See application file for complete search history.

(56) References Cited

U.S. PATENT DOCUMENTS 10,507,263 B2 * 12/2019 Nazhat .................... C03C 11/00
2002/0120348 A1    8/2002 Melican et al.
(Continued)

FOREIGN PATENT DOCUMENTS

CN    1857742 A1    11/2006
CN    919361 A1    2/2007
(Continued)

OTHER PUBLICATIONS

International Search Report and Written Opinion mailed Nov. 16, 2020, from International Application No. PCT/EP2020/073515, 15 pages.
(Continued)

*Primary Examiner* — Wayne A Langel
(74) *Attorney, Agent, or Firm* — Meunier Carlin & Curfman LLC

(57) ABSTRACT

The present application provides biodegradable composite material comprising bioresorbable magnesium or magnesium alloy embedded in bioresorbable glass fiber reinforced polymer matrix, and a bioresorbable implant comprising the composite material. The present application also provides use of the composite material, and methods for preparing the composite material and a medical device of a part thereof.

22 Claims, 5 Drawing Sheets

(51) Int. Cl.
*A61L 27/10* (2006.01)
*A61L 27/34* (2006.01)
*A61L 31/02* (2006.01)

(52) U.S. Cl.
CPC .......... *A61L 31/022* (2013.01); *A61L 31/026* (2013.01); *A61L 2300/604* (2013.01)

(56) References Cited

U.S. PATENT DOCUMENTS

| | | | | |
|---|---|---|---|---|
| 2008/0051335 | A1* | 2/2008 | Kleiner | A61K 9/143 514/8.1 |
| 2014/0271785 | A1* | 9/2014 | Bagga | A61L 27/56 424/490 |
| 2014/0277578 | A1 | 9/2014 | Day et al. | |
| 2015/0306282 | A1* | 10/2015 | Scanlon | A61L 31/18 623/1.34 |
| 2015/0374521 | A1* | 12/2015 | Zheng | A61F 2/915 623/1.2 |
| 2017/0273680 | A1* | 9/2017 | Sengun | A61L 31/044 |
| 2019/0099515 | A1* | 4/2019 | Bagga | A61L 27/56 |

FOREIGN PATENT DOCUMENTS

| | | | | |
|---|---|---|---|---|
| CN | 105377318 | A | | 3/2016 |
| CN | 105797214 | A | | 7/2016 |
| CN | 106149127 | A | | 11/2016 |
| CN | 107106210 | A | | 8/2017 |
| CN | 107224616 | A | | 10/2017 |
| CN | 108066822 | A1 | | 5/2018 |
| EP | 2243749 | A1 * | 10/2010 | A61L 27/10 |
| EP | 2568928 | B1 | 9/2015 | |
| EP | 3470097 | A1 * | 4/2019 | A61B 17/80 |
| JP | 2008307842 | A | 12/2008 | |
| JP | 2013006293 | A | 1/2013 | |
| WO | 2006114483 | A2 | 11/2006 | |
| WO | 2008092192 | A1 | 8/2008 | |
| WO | WO-2017155956 | A1 * | 9/2017 | A61L 27/46 |
| WO | WO-2020044327 | A1 * | 3/2020 | A61B 17/80 |

OTHER PUBLICATIONS

International Preliminary Report on Patentability dated Jan. 3, 2022, issued in International Application No. PCT/EP2020/073515, 11 pages.
Written Opinion of the International Preliminary Examining Authority mailed Sep. 30, 2021, issued in International Application No. PCT/EP2020/073515, 10 pages.
Xiaoling Liu et al., "Mechanical, degradation and cytocompatibility properties of magnesium coated phosphate glass fibre reinforced polycaprolactone composites", Journal of Biomaterials Applications, vol. 29, No. 5, Jul. 14, 2014, 14 pages.
Xiaoling Liu et al., "Magnesium coated phosphate glass fibers for unidirectional reinforcement of polycaprolactone composites : Magnesium-Coated Unidirectional Phosphate Glass Fiber", Journal of Biomedical Materials Research Part B, Applied Biomaterials, vol. 103, No. 7, Nov. 18, 2014, 9 pages.
Anna Morawska-Chochol et al., "Magnesium alloy wires as reinforcement in composite intramedullary nails", PubMed, Biomed Mater Eng. 2014, 24(2), 1507-1515, Jan. 1, 2014, XP055747282, Retrieved from the Internet: URL:https://pubmed.ncbi.nlm.nih.gov/24642977/, 1 page.
Notification of First Office Action and Search Report, issued Jun. 13, 2022, in corresponding CN application 2020800583494, 21 pages.
"China magnesium industry progress", Meng Shukun, first edition, pp. 114-128, Metallurgical Industry Press Published Dec. 31, 2012.
Notification of second office action from National Intellectual Property Adiminstration, PRC in regards with copending Chinese application CN2020800583494.Issued on Dec. 6, 2022 23p.

* cited by examiner

COMPOSITE MATERIAL, IMPLANT COMPRISING THEREOF, USE OF THE COMPOSITE MATERIAL AND METHODS FOR PREPARING THE COMPOSITE MATERIAL AND A MEDICAL DEVICE

CROSS REFERENCE TO RELATED APPLICATIONS

This application is a United States National Phase Patent Application of International Patent Application Number PCT/EP2020/073515, filed on Aug. 21, 2020, which claims the benefit of priority to EP Application Serial No. 19397525.7, filed Aug. 21, 2019, both of which are incorporated by reference herein in their entirety.

FIELD OF THE APPLICATION

The present application relates to biodegradable composite material comprising bioresorbable magnesium or magnesium alloy embedded in bioresorbable glass fiber reinforced polymer matrix, to a method for preparing thereof and to a bioresorbable implant comprising the composite material. The present application also relates to use of the composite material, and to a method for preparing a medical device of a part thereof.

BACKGROUND

For orthopaedic applications current biomaterials such as titanium and its alloys, stainless steel and Co—Cr are the preferred metal implant materials, they are relatively inert in the body, meaning that they exhibit little host response, positive or negative, and those are not designed to degrade safely in the body. However, all surgically implanted metal alloys undergo some electrochemical degradation due to the complex and corrosive environment of the body. Combined with significant wear that can occur in load bearing applications, particles of the implant can be released into the surrounding tissues, causing discomfort and potential health risks. In addition, this wear and corrosion can lead to the need for a second implant during the patient's lifetime. Although the bulk material may be considered bioinert, the way in which the particles are metabolized within the body can lead to acute inflammation and eventually implant failure. Moreover, their mechanical properties are generally poorly matched with those of bones i.e. the strength and stiffness of these metals many magnitudes higher than cortical bone and consequently many times leads to the adverse events related to stress shielding phenomena. Stress shielding is an adverse long-term effect which leads to decreased bone strength. The metal implant has a much higher stiffness than bone, and therefore are less likely to deform under the stress load-bearing activities. By absorbing the majority of the load, the implant reduces the mechanical force transmitted to the bone itself. Since bone requires continual mechanical stimulation to remodel and regrow, a stress-shielded implant site will gradually lose bone density, known as bone resorption; this phenomenon is especially prevalent in the medial proximal femur, known as the calcar region. This decreased bone density may lead to aseptic loosening and stem migration, as well as periprosthetic fractures. Furthermore, polymers for orthopaedic applications generally do not offer sufficient mechanical strength for such applications and are often associated with "foreign body reaction". Additionally, bioresorbable polymers degrade by hydrolysis, and an acidic pH environment can be created which may enhance osteoclast genesis to the detriment of osteoblast genesis [Arnett 2008]. The field requires new biomaterials to solve above mentioned problems.

The field of biomaterials is constantly expanding and evolving, therefore even defining the term "biomaterial" is not a simple task. In the '80s, the American National Institute of Health (NIH) proposed the following definition: "any substance (other than a drug) or combination of substances, synthetic or natural in origin, which can be used for any period of time, as a whole or as a part of a system which treats, augments, or replaces any tissue, organ, or function of the body". The evolution of the definition of 'biomaterial' is closely linked to the development of biomaterials themselves. The first generation of biomaterials were mainly designed to match the mechanical, chemical, and physical requirements of their applications, with minimal toxic responses. However, biomaterials are not inert, and increased understanding of material toxicity led to the demand for greater biocompatibility. For example, titanium and its alloys are one of the most commonly used biomaterials for orthopaedic applications. Negative effect of the stress-shielding is continuing to decrease bone quality, also after the bone has healed, as long as the rigid implant is present. Moreover, during the lifetime of the implant wear debris is produced, which could induce osteolysis, a major cause of orthopaedic-implant aseptic loosening. Alloys have been developed and a wide variety of surface treatments have been employed to overcome these inconveniences. Furthermore, the notion of "foreign body reaction" (late stage of inflammation and wound healing reactions leading to implant encapsulation), as well as the concept of osseointegration or osteoinduction, emphasized the need for a deeper understanding of the interaction between biomaterials and surrounding/living tissues. Combined research efforts led to the development of a second generation of biomaterials that can be divided into two classes: (1) "resorbable", meaning that they should be able to maintain mechanic integrity until the tissue regains its own stability, thereafter being absorbed by the body, and (2) "bioactive" i.e., able to elicit a specific tissue response or to strengthen the intimate contact between the implant and the osseous tissue. Bioactive glass or calcium phosphates (e.g., hydroxyapatite) as ceramics or as metal coatings, grafting of peptides or phospholipids onto metal surfaces or porous structures, and the development of resorbable polymers such as chitosan and polylactide are some of the strategies which have been used. The newest, third generation of biomaterials ("smart" materials) aim combine bioactivity and biodegradability i.e. bio-resorbability and should elicit specific cellular responses at the molecular level).

Bioactive composite materials may be present as both solid and porous systems with the bioactive phase incorporated either as filler or reinforcement into the bioresorbable polymer matrix. It is possible to obtain high-strength composite structures for the regeneration of human bone at load-bearing sites. However, with regard to their mechanical properties in comparison to human cortical bone, conventional polymer/glass composites have revealed insufficient stiffness and flexural modulus and strength retention to carry the load over the healing period of the bone in truly load-bearing applications such as intramedullary nails or spinal cages.

There is a need for third generation biomaterials that could provide bioresorbable implants, which have mechanical properties more similar to bones.

SUMMARY

Surprisingly it has been now found that combining reinforcing bioresorbable magnesium or magnesium alloys with bioresorbable glass fiber reinforced polymer matrix i.e. forming a hybrid composite, the major drawbacks in mechanical properties, as presented in prior art, of both materials can be overcome and moreover the corrosion rate of the magnesium can be controlled by bioresorbable glass fiber reinforced polymer matrix. This hybrid composite material can fulfill the requirements of third generation biomaterials in the medical field for the load-bearing tissue-engineering. Same way the hybrid composite serves as a solution for current problems in the technical field where environmental control and pollution prevention requires sustainable solution with fully degradable strong material which can be used in structural parts and degraded after life cycle of the product without leaving any harmful and toxic by-products left in the nature.

It is possible to obtain medical products having desired properties and behaviour. For example the products may be arranged to deteriorate in a controlled way, such as during a predefined period of time, in a body, and the degradation products may be bioabsorbed.

Also the mechanical properties of the products are suitable for medical uses, but also for other uses wherein properties such as light weight, formability and mechanical strength and other mechanical properties are required, such as in objects and structures in vehicles and sports equipment.

The present application provides a method for preparing biodegradable composite material, the method comprising
providing magnesium or magnesium alloy in a reinforcing form,
providing bioresorbable glass fibers,
providing bioresorbable polymer,
combining the materials to form biodegradable composite material comprising bioresorbable magnesium or magnesium alloy in a reinforcing form embedded in bioresorbable glass fiber reinforced polymer matrix.

The present application provides biodegradable composite material comprising bioresorbable magnesium or magnesium alloy in a reinforcing form embedded in bioresorbable glass fiber reinforced polymer matrix. This composite material may be obtained with the methods disclosed herein.

The present application also provides a bioresorbable implant comprising the composite material.

The present application also provides use of the composite material in the manufacture of a medical device, such as an implant.

The present application also provides use of the composite material in the manufacture of primary structures in commercial, automotive, industrial, aerospace, marine, and recreational structures. The present application also provides such medical devices, primary structures and other objects disclosed herein comprising the composite material.

The present application also provides a method for preparing a medical device or a part thereof, the method comprising
providing biodegradable composite material comprising bioresorbable magnesium or magnesium alloy in a reinforcing form embedded in bioresorbable glass fiber reinforced polymer matrix,
providing one or more processing device,
processing the composite material with the processing device into a medical device or a part thereof.

The main embodiments are characterized in the independent claims. Various embodiments are disclosed in the dependent claims. The embodiments and examples recited in the claims and in the specification are mutually freely combinable unless otherwise explicitly stated.

The present hybrid composite materials are suitable for application requiring certain mechanical properties, such as resistance for compression and/or tension.

The present hybrid composite materials are suitable for several medical treatment methods and application, especially ones involving bones and/or implanting. The materials exhibit similar mechanical properties as the bones to be treated. For example the composite materials have similar compression strength as cortical bones, unlike commonly used materials such as titanium-based materials.

The present hybrid composite materials also exhibit efficient bioactivity, such as osteoinductive properties. This is important in several applications, such as in cases wherein regeneration of bone is desired, for example when medical products are inserted in spine.

The present composite materials are also fully biodegradable and bioresorbable, so that all the materials used in the composite will be substantially degraded in body, and the degradation products will be metabolized in a safe manner, i.e. bioresorbed. There is no need to remove the biodegradable products, such as implants, from the body, and therefore unnecessary surgeries or other medical treatments such as anaesthesia can be avoided, which is especially important with high risk patient group, such as paediatric or geriatric patients or patients with poor condition.

DETAILED DESCRIPTION

Figure 1:
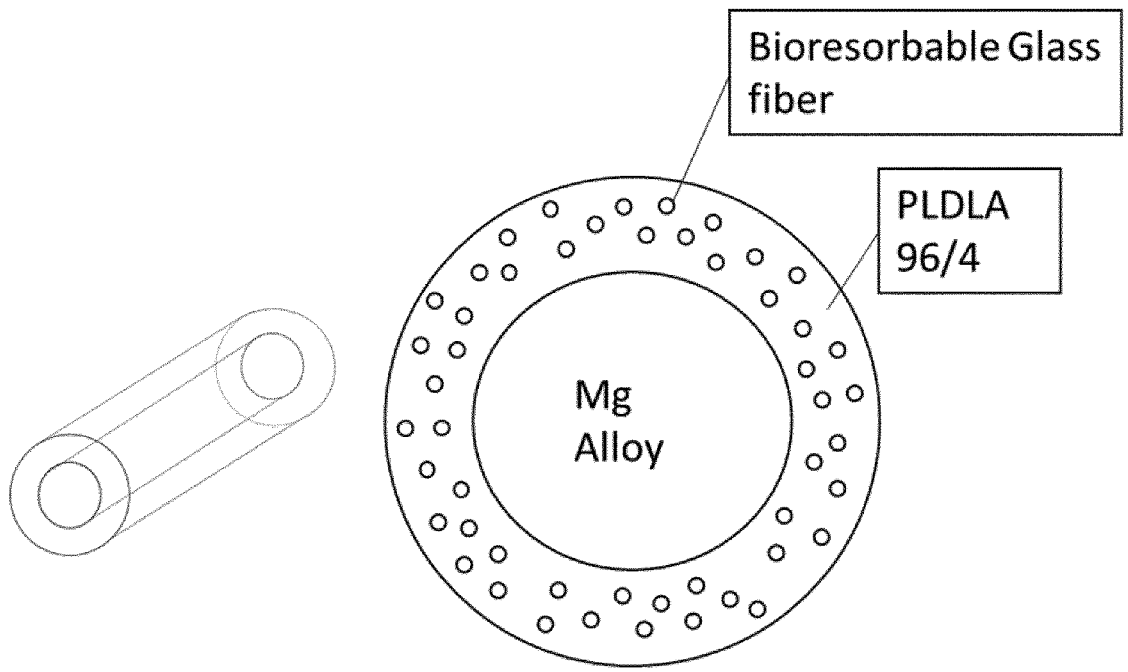
FIG. 1 shows a schematic example of a round rod of hybrid composite material obtained by machining a magnesium alloy rod and bioresorbable glass fiber unidirectionally reinforced PLDLA rod

In this specification, if any numerical ranges are provided, the ranges include also the upper and lower values. The open term "comprise" also includes a closed term "consisting of" as one option.

The present application relates generally to hybrid composites, and more particularly, to a hybrid composite of magnesium or magnesium alloy with glass fiber reinforced polymer matrix that have a solubility or decomposability in water or physiological medium to permit degradation and/or recyclability of the composite in a natural environment Unless defined otherwise, all technical and scientific terms used herein have the same meaning as commonly understood by one of ordinary skill in the art to which the invention belongs.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

The phrases "percent by weight" and "by weight" or "wt %", as used herein, are intended to be defined as the percent by weight of the total expressed composition, unless otherwise explicitly stated. Additionally, as used herein, the terms "weight percent" and "percent by weight" may be used interchangeably and are meant to denote the weight percent (or percent by weight) based on the total expressed composition.

The term "bioresorbable" refers to material which in contact with natural environment such as soil or compost or biological tissues and/or physiological fluids will, following placement, degrade, resorb and/or absorb into the environment while maintaining its mechanical properties for a certain period of time.

The terms "bioresorbable", "biodegradable", "biosoluble", "bioabsorbable", biocorridible and "bioerodible" with or without prefix "bio" may be used interchangeably herein.

The terms "bioresorbable glass fiber", "bioresorbable fiber", "bioglass fiber", "controlled lifetime glass fiber", "alterable glass fiber", "glass fiber", and "fiber" may be used interchangeably herein.

The term decomposability is defined here as (biology) to break down (organic matter) or (of organic matter) to be broken down physically and chemically by bacterial or fungal action; (chemistry) to break down or cause to break down into simpler chemical compounds or to break up or separate into constituent parts.

The "hybrid composite" is defined so that hybrid composite material is fabricated or obtained by combining two or more different types of reinforcement with single polymer matrix, where polymer matrix can be continuous or discontinuous containing one or more polymers.

The present application relates generally to hybrid composites, and more particularly, to composite of magnesium or magnesium alloy with glass fiber reinforced polymer matrix that have a solubility and/or decomposability in water or physiological medium to permit degradation and/or recyclability of the composite in a natural environment.

Herein and hereafter "optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The present application relates to magnesium-containing composite materials, and to product containing or comprising the composite material, including implants and other objects. The main benefits of the implants are (1) avoidance of second or revision surgery, therefore decreased patient morbidity, the risk of new symptoms developing, and health care costs, (2) temporary support during tissue recovery, (3) possible inherent repair (i.e., osteoinduction) and (4) malleability, which allows surgeon to shape the implant by bending it according to the bone's anatomy and shape before insertion. Due to the magnesium-alloy's metallic, plastic nature the new shape will stay unchanged during the healing period.

Despite significant recent research, there have been challenges in the prior art to the successful implementation of magnesium based materials in a variety of applications. Many of these challenges are related to corrosion, be it rate, morphology or products, which can be now solved according to current invention of hybrid composite. However, the present application provides a hybrid composite material with mechanical benefits of a metal combined with the degradable and biological advantages displayed by polymers and synthetic biomaterials.

In general bioresorbable magnesium or magnesium alloy implantable materials do not come without severe concerns. Pure magnesium is incapable of providing the necessary mechanical and corrosion properties required for a wide variety of implant applications, even though pure Mg has an flexural modulus of 45 GPa, which is much closer to that of human cortical bone (15-20 GPa) than most common Ti alloys (110-120 GPa) but magnesium may still be prone to stress shielding. The main concern of using magnesium as an implant material has been mainly its mechanical strength throughout its degradation i.e. strength retention and inherent property to produce hydrogen gas while degrading, leading to the formation of gas cavities in vivo, both related to magnesium corrosion i.e. resorption rate. Therefore, potential alloying elements have been considered and corrosion rates as well as mechanical properties have been tried to solve by tailoring different factors such as magnesium purity, the choice of alloying elements, the metal microstructure, and the material processing route. A potential alloying system for magnesium especially for orthopedic applications has been suggested in prior art to increase the mechanical and corrosion properties of magnesium. The most widely studied alloying elements are rare-earth elements (such as yttrium and gadolinium), zirconium, manganese, zinc, calcium, lithium, aluminum and strontium, among others. The alloying elements, in addition to the potential harm of hydrogen evolution and soluble (or insoluble) corrosion products, may contain new elements of unknown toxicity like the biocompatibility of the rare-earths, which still remains a question of debate. However, even elements normally present in the body (e.g. Zn, Ca and Mn) can also be toxic if the release rate is too high as the levels cannot be dealt with appropriately (e.g. excess Mg via kidneys, hydrogen gas via soft tissues). Thus, a truly biocompatible Mg alloy is required to avoid the use of toxic alloying elements and ensure an appropriate release rate for other elements, even those which are naturally occurring.

Alloying can further improve the general corrosion behavior, but it does not change galvanic corrosion problems if magnesium is in contact with another metal and an electrolyte and cannot be used as pure. Therefore, it is necessary to develop coatings or surface modification to slow the degradation rates of various Mg alloys. Coatings for biomaterials, especially biodegradable magnesium, have the same requirements as the base materials themselves of being biocompatible and fully degradable. The latter point is particularly salient for understanding what occurs over the implant life cycle. In the case of magnesium, coatings themselves cannot be perfect barriers to corrosion (which would be the goal of a coating system on a structural material). To allow an Mg implant to biodegrade, the coatings must, at some stage, cease to be a corrosion barrier, although they may be required to provide an effective method to reduce the initial corrosion rate of the bare metal so the surrounding bone tissue (in the case of orthopedics) may start to form. Ideally, the coating would itself degrade gradually, helping to control the overall corrosion process while leaving no harmful traces. There are a large number of possible coating technologies for Mg biomaterials, including anodization, metal-metal coatings, plasma spray, chemical vapor deposition, atomic layer deposition, pulsed laser deposition, ion beam assisted deposition, solution, emulsion and suspension coatings, calcium phosphate (CaP) deposition achieved by various means and the well-known methods of electrodeposition and conversion coating. Moreover, the galvanic corrosion problem can only be solved by proper coating systems, but chemical conversion coatings are just a few micrometers thick and thus they are only offering a limited protection.

The present functional bioresorbable implants based upon magnesium and magnesium alloys provide the mechanical benefits of a metal combined with the degradable and biological advantages displayed by polymers and synthetic biomaterials. In developing the materials there were challenges in the successful implementation of magnesium-based materials in a variety of applications in the body. Many of these challenges were related to corrosion, be it rate, morphology or products.

Third generation biomaterials disclosed herein are based on combining bioactive inorganic materials with biodegradable polymers. They contain bioresorbable glass fiber reinforced polymer composite materials, where glass fiber and polymer matrix are both degradable i.e. bioresorbable in natural environment, such as in nature or in human body. Glass fibers can be manufactured from bioresorbable and biocompatible glasses, such as glasses presented in EP2243749B1, US5108957A, WO2012001449A1 and EP0802890B1.

Bioresorbable and bioactive glasses have a capability of reacting with physiological fluids forming tenacious bonds to bone through the formation of bone-like hydroxyapatite layers leading to effective biological interaction and fixation of bone tissue with the material surface. Moreover, in the case of silicate and phosphate bioactive glasses reactions on the material surface induce the release and exchange of critical concentrations of soluble Ca, P and Na ions, which can lead to favorable intracellular and extracellular responses promoting rapid bone formation. Many bioresorbable glass compositions have been developed over the years to contain no sodium or to have additional elements incorporated in the silicate or phosphate network such as fluorine, magnesium, strontium, iron, silver, boron, potassium, zinc, copper, barium, lithium or combinations of those. Fabrication techniques for bioactive glasses or glass fibers include both traditional melting methods and sol-gel techniques. The typical feature common to all bioactive glasses, being melt or sol-gel derived, is the ability to interact with living tissue, in particular forming strong bonds to bone (and in some cases soft tissue, a property commonly termed bioreactivity or bioactivity, as mentioned above. For establishing bond with bone, such a biologically active apatite, a surface layer must form at the material/bone interface. Thus, one basis of the bone bonding property of bioactive glasses is the chemical reactivity in physiological body fluids (in vitro and in vivo), which may result in the formation of a hydroxycarbonate apatite (HCA) layer to which bone can bond. Briefly, the processes on the glass surface are characterized by ion leaching/exchange, dissolution of the glass network and precipitation and growth of a calcium-deficient carbonated apatite (HCA) surface layer, whereas cellular reactions include colonization, proliferation and differentiation of relevant (bone) cells.

The bioactive glasses presented in previous exhibit several advantages in comparison to other bioactive ceramics, e.g., sintered hydroxyapatite, in tissue engineering applications. Polymer/bioceramic composite materials represent a convenient alternative due to the possibility to tailor their various properties (e.g., mechanical and structural behavior, degradation kinetics and degree of bioactivity). Composites made of polymers and bioceramics may combine the advantages of their singular components. Polymers exhibit generally high ductility, toughness, favorable formability as well as processability and plasticity. The glass or glass-ceramic phase adds stiffness and mechanical strength to the composite. In particular, composites based on biodegradable polymers may be useful as bone tissue engineering materials because this particular combination does not require a revision surgery for their removal as newly formed bone gradually substitutes the implanted material during degradation.

Composite Material

The (hybrid) composite material comprise (pure) magnesium or magnesium alloys combined or embedded with bioresorbable glass fiber reinforced polymer matrix. It may further comprise a coating on the surface of the magnesium or magnesium alloy, preferably to act as an adhesion layer to bioresorbable glass fiber reinforced polymer matrix and/or to act as further layer to slow down hydrogen gas evolution. It may also act as a hydrogen trap, which prevents hydrogen release from the structure, and/or it may keep corrosion products on the magnesium alloy's surface forming corrosion inhibiting layer.

The present application thus provides composite materials that are useful as structural fixation for load-bearing purposes, exhibiting improved mechanical properties as a result of hybrid composite structure, unlike the composites of prior art. Indeed, the disadvantages of the prior art are overcome or at least minimized by the solutions of the present application, which provides hybrid composite materials wherein magnesium or magnesium alloy is combined or embedded with bioresorbable glass fiber polymer matrix.

The present application provides a hybrid composite material in which the drawbacks of the prior art materials can be minimized or even eliminated, i.e. the composite retains its strength and modulus in vivo for example for a time period sufficient for bone fracture healing. Indeed, high strength and flexural modulus matched with cortical bone with good strength retention in vivo conditions can be achieved through combining two bioresorbable reinforcement, magnesium/magnesium alloy and glass fiber into bioresorbable polymer matrix. Mechanical strength as used here includes bending strength, torsion strength, impact strength, compressive strength and tensile strength.

The present application provides a hybrid composite material, which is malleable i.e. surgeon can shape the implant by bending it according to the bone's anatomy and shape before inserting it. Due to the hybrid composite materials' metallic, plastic nature the new shape will stay unchanged during the healing period.

The present application also provides preparation methods that allow control over chemical and physical strength and stability of the hybrid composite material. The strength and stability of the hybrid composite can be modified either by changing the magnesium alloying system, by changing optional chemical coating on the magnesium or magnesium alloy, by changing bioresorbable glass fiber composition and/or by changing bioresorbable polymer matrix or by combination and relative ratio(s) of these.

One way to modify strength and stability is to use magnesium or magnesium alloys in different forms such as a rod, a plate, a core, a tube or fibers or other physical form or shape which brings a reinforcing effect to the hybrid composite and embedded by bioresorbable fiber reinforced polymer matrix. Another way is to use bioresorbable glass fiber either continuous or discontinuous in a bioresorbable polymer matrix.

The present application provides a method for preparing biodegradable composite material, the method comprising
providing magnesium or magnesium alloy in a reinforcing form,
providing bioresorbable glass fibers,
providing bioresorbable polymer, and
combining the materials to form biodegradable composite material. The composite material is fully or substantially fully biodegradable.

The magnesium or magnesium alloy is provided in a reinforcing form, which means that it is present as a reinforcement, which can provide mechanical support and is self-supporting, for example it is not provided and/or present as a coating on a different material. The reinforcing form of magnesium or magnesium alloy may be in a form of a rod, a plate, a core, a tube or fibers or other reinforcing shape. The reinforcing form of magnesium or magnesium alloy may therefore act as a core, such as in the examples of FIGS. 1-5 and 7A and 7B, and it is embedded, such as mixed, covered or coated, with the bioresorbable glass fibers and the bioresorbable polymer. When the magnesium or magnesium alloy is present or provided as a tube it may be desired not to fill the aperture of the tube with any substance but it may be left unfilled to allow use of suitable handling during applying and/or removing the product into or from a body.

The bioresorbable glass fibers and bioresorbable polymer may be first combined and subsequently combined with the reinforcing form of magnesium or magnesium alloy. The bioresorbable glass fibers and bioresorbable polymer may be provided as a ready-made product, i.e. a glass-fiber-polymer composite, for example as a tape, a filament, a yarn, a machined object and/or as a moldable composite material. The glass-fiber-polymer composite may be further heated, pressed and/or otherwise processed and/or reacted to form it into a desired form, i.e. combined with the magnesium or magnesium alloy. For example the glass-fiber-polymer composite may be heated before and/or during applying onto the reinforcing form of magnesium or magnesium alloy. The glass-fiber-polymer composite is preferably heated to obtain a melt of the polymer. The polymer should be melted in such degree that it becomes mouldable. After the glass-fiber-polymer composite is applied, it will be cooled or let to cool to solidify the melt.

It is also possible to have a different combination order, for example the reinforcing form of magnesium or magnesium alloy may be first combined with the bioresorbable polymer and subsequently combined with the bioresorbable glass fibers.

In one embodiment the method comprises
combining the bioresorbable glass fibers and the bioresorbable polymer to obtain bioresorbable glass fibers in a bioresorbable polymer matrix, and
combining the bioresorbable glass fibers in a bioresorbable polymer matrix with the reinforcing form of magnesium or magnesium alloy to form the biodegradable composite material.

In one embodiment the method comprises
combining the reinforcing form of magnesium or magnesium alloy and the bioresorbable polymer to obtain reinforcing form of magnesium or magnesium alloy in a bioresorbable polymer matrix, and
combining the reinforcing form of magnesium or magnesium alloy in a bioresorbable polymer matrix with the bioresorbable glass fibers to form the biodegradable composite material.

Any suitable combining methods or combinations thereof may be used, such as one or more selected from applying, compressing, melting, laminating and polymerizing. In most cases it is necessary to provide the polymer(s) or precursor(s) thereof in a mouldable state, such as molten or flowable state, so that the polymer may form a matrix around the glass fibers and/or magnesium or magnesium alloy.

When combining the ingredients, in some methods it is necessary to obtain or form a melt, more particularly a melt of the bioresorbable polymer. This can be achieved by using increased temperature, such as a temperature at the melting point of the bioresorbable polymer or higher. The bioresorbable polymer may be or comprise thermoplastic polymer. The melt polymer is then combined and/or mixed with the glass fibers and/or the magnesium or magnesium alloy.

In such way it is possible to combine the polymer with the other ingredient(s), so that a mixture is formed, which may be called a composite material, wherein the polymer is present as a matrix. It is possible to obtain the polymer or polymer matrix by providing a precursor of the polymer or polymer matrix, such as monomers, oligomers and/or polymers, which are formed into the desired polymer by using suitable reaction, such as polymerization reaction. A polymerization initiator may be provided, such as a chemical initiator, (UV) light, other radiation and/or heat.

Pressure may be applied during combining, such as by compressing with a suitable device, which pressure may cause the polymer(s) or precursor(s) therefore to become mouldable. Heat may be also used, which may be external heat and/or heat caused by applying the pressure.

Figure 2:
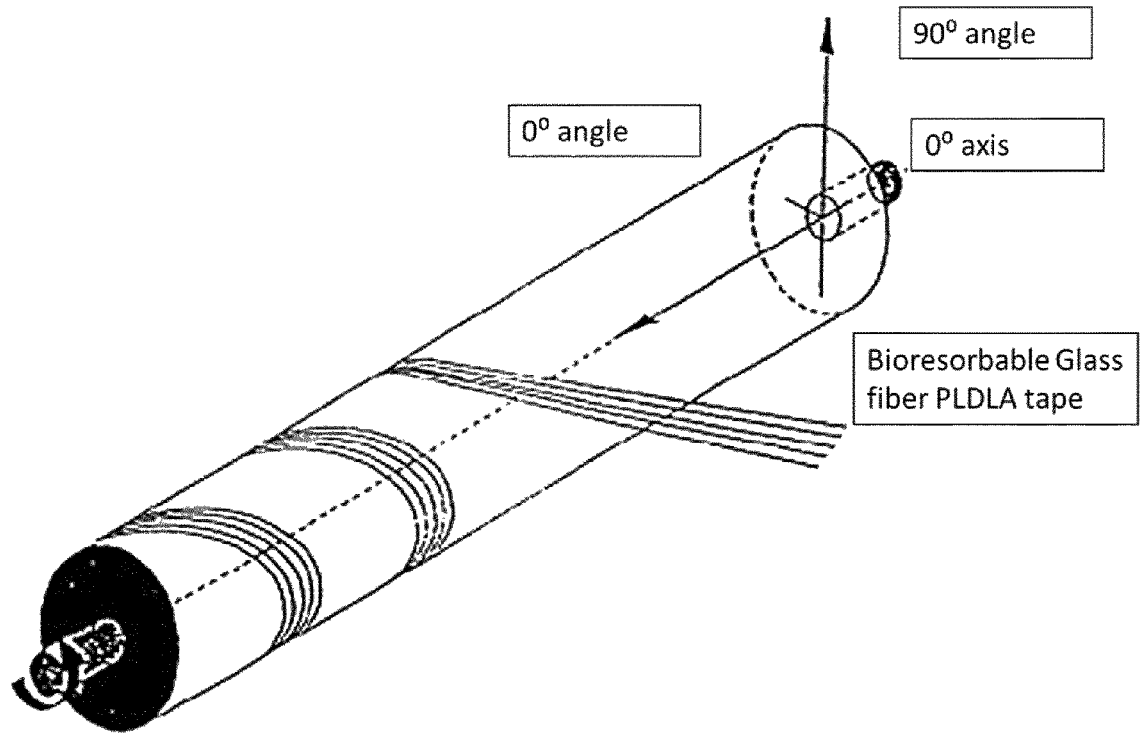
FIG. 2 shows a schematic example of a round rod of hybrid composite material obtained by tape winding bioresorbable glass fiber around a magnesium alloy rod

When the reinforcing form of magnesium or magnesium alloy is provided as a core or the like structure, the bioresorbable glass fibers and the bioresorbable polymer may be provided to cover this self-supporting structure, for example by winding, such as by filament winding or tape winding, as shown in FIG. 2 wherein glass fiber-polymer tape is wound onto a magnesium core, or by providing a melt of the bioresorbable glass fibers in a bioresorbable polymer matrix onto the reinforcing form of magnesium or magnesium alloy by using any suitable method such as by kneading, by extruding including coextrusion and thermoplastic pultrusion, by injection moulding or by any other devices and methods disclosed herein. Magnesium part and/or glass fiber in polymer matrix part may be provided as objects machined to fit each other, and then applied to combine and form a composite structure. For example a rod of magnesium alloy may be applied into an aperture in a glass-fiber-polymer tube or other suitable structure adapted to receive said rod. The fitting shall be preferably a tight fitting, such as a fitting requiring compression during applying so that the rod is forced into the aperture, thus resulting in a compressive contact between the two objects. A structure such as shown in FIG. 1 may be obtained by using such methods.

Magnesium or alloy thereof may be first processed and/or machined into a desired form for combining with the other ingredients by using any suitable processing or machining devices, such as by mechanical machining, laser machining, pressing, water jet processing, additive manufacturing, such as including providing the biodegradable magnesium alloy as powder, granules or as a wire, or injection molding, such as by thixotropic molding, liquid metal molding or metal injection molding, or by combinations thereof. After this processing and/or machining a suitable form, such as a rod, a plate, a core, a tube or fibers or other physical form or shape can be obtained.

The bioresorbable glass fibers may be provided in continuous form and/or in discontinuous form. Also the reinforcing form of magnesium or magnesium alloy may be provided in continuous form and/or in discontinuous form.

According to one embodiment the hybrid composite material comprises two or more types magnesium alloys, each type having different composition, or comprise a second bioresorbable metal besides of primary magnesium or magnesium alloys such as zinc or iron including their alloys. The metals, or types of metals, which may be magnesium, magnesium alloy or other metal or alloy thereof, may be called as a first metal, a second metal and optionally a third or further metals(s) by running number. A second type of resorbable metal can be for example metal or alloy having higher resorption rate or different mechanical properties, which can be in the form of granules, spheres, blocks or fibers.

According to one embodiment the hybrid composite material comprises two or more types of resorbable and biocompatible glasses or glass fibers, each type having a different composition, resorption rate and/or bioactivity. The glasses, or types of glasses, may be called as a first glass, a second glass and optionally a third or further glass(es) by running number. A second type of glass can be for example a glass having higher bioactivity and resorption rate. In the case of a faster resorption rate and a higher bioactivity, the main function is not the reinforcement of the composite, but instead to be a more osteoconductive or antimicrobial material, which means that it promotes and facilitates bone healing, in the form of granules, fibers and/or powder, such as for example BonAlive® S53P4 glass. The different types of glasses may be for example different types selected from silica, phosphate, boron and magnesium based bioresorbable glasses.

The composite material may also comprise two or more types of bioresorbable polymers, two or more types of chemical coatings or partial coating/coatings, coatings with pattern or coatings with the variable thickness, which provide design specific optimized/programmed corrosion rate or adhesion behavior. Moreover, the composite material may also comprise the glass in the form of two or more groups of fibers having different median diameters.

The composite materials disclosed herein may be called as hybrid composite materials. The term hybrid composite as is used in this description refers materials that are the result of a combination of several phases where at least two reinforcement elements are integrated into a matrix to improve the composite's properties i.e. hybrid composites can be defined as the materials that comprise or consist of two or more types of reinforcements embedded in a single polymer matrix. The morphology, nature, and orientation of components are significantly affecting the manner that the composite reacts against external loads. In fact, the properties of the composite are closely linked to its internal structures, which are governed by the characteristic properties of the constituent elements of the hybrid composite. The mechanical properties of hybrid composites consist of n (n>2) jointly working phases, which are very important. However, the mechanical behavior of hybrid composites depends not only on the character of a matrix and reinforcements but also on properties of the interface between these components and the matrix, which must be taken into consideration. Since hybrid composites use more than one kind of reinforcement in the same matrix; hence, the idea is to get the synergistic effect of the properties of reinforcements on the overall properties of composites. With hybrid composites it may be possible to have greater control of the properties, achieving a more favorable balance between the advantages and disadvantages inherent in any composite material. Furthermore, the positive hybrid effect could be noticed in such materials as the load could still be bridged to the surrounding high elongation reinforcement (magnesium or magnesium alloy) upon the fracture of the reinforcements having low elongation (glass fiber), thus resulting in enhanced mechanical properties of the composites.

In fact, hybrid composites can be considered as the weighted sum of the individual constituents in which a balance of advantage and disadvantages of the constituents shall be achieved. It is identified that the advantages of one reinforcement could complement the disadvantages of another reinforcement through the hybridization like according to this invention magnesium or magnesium alloys with higher stiffness and flexural modulus complements the bioresorbable glass fiber reinforced polymer matrix stiffness and flexural modulus. Similarly, bioresorbable glass fiber reinforced polymer matrix complements the strength properties of magnesium and magnesium alloy. Therefore, hybrid composite made from magnesium or magnesium alloy and bioresorbable glass fiber reinforced matrix yields optimal strength, stiffness and modulus, what is required from load-bearing implant or structural material.

The properties of a hybrid composite can be influenced by the orientation of the reinforcements, reinforcement content and length, layering patterns of the two reinforcements, their intermingling capacities, reinforcement-to-matrix interface, and also the failure strain of single reinforcements.

According to one embodiment the hybrid composite has a flexural strength of 200-1500 MPa, more preferably 300-800 MPa or 300-500 MPa, and most preferably 400-500 MPa measured by ISO 178:2019 or ASTM D790-17.

According to another embodiment the hybrid composite has a flexural modulus of 20-40 GPa, more preferably 25-35 GPa and most preferably about 30 GPa measured by ISO 178:2019 or ASTM D790-17.

According to another embodiment the hybrid composite has a shear strength of 4000-5000 N, more preferably 4200-4800 N, measured by BS 2782-3 method 340A-B (rate 10 mm/min).

The hybrid composite may retain at least 60% of its mechanical properties in physiological conditions (in vitro, temperature 37° C.) at least for 3 months, preferably for 4-5 months and most preferably for 6 months measured by ISO 178:2019 or ASTM D790-17.

The present application also relates to the use of the hybrid composite material in the preparation or manufacture of a medical device. The present application also relates to a medical device comprising the hybrid composite material as explained herein. The medical device may be for example an implant. The medical devices manufactured from the composite, having high strength, modulus just above cortical bone and retention of those properties in vivo are useful in manufacturing of e.g. bone fracture fixation devices, because aforementioned properties yield the same design freedom and the usability as current inert biometals, such as titanium and its alloys under hydrolytic conditions.

The medical device may be any kind of implant used within the body or a device for supporting the tissue or bone healing and/or regeneration.

An implant according to the present context may comprise any kind of implant, more particularly a (fully) bioresorbable implant, which may be used for surgical musculoskeletal applications, such as a screw, a plate, a pin, a tack or a nail, for the fixation of bone fractures and/or osteotomies to immobilize the bone fragments for healing; a suture anchor, a tack, a screw, a bolt, a nail, a clamp, a stent and other devices for bone-to-bone, soft tissue-to-bone, soft tissue-into-bone and soft tissue-to-soft tissue fixation; devices used for supporting tissue or bone healing or regeneration; or cervical wedges and lumbar cages and plates and screws for vertebral fusion and other operations in spinal surgery.

In some further examples the implant comprises a nail, such as intramedullary nail, for the fixation of bone fractures and/or osteotomies to immobilize the bone fragments for healing, a clip, a staple, a mesh, a scaffold, a cage, or a Kirschner wire.

The present hybrid composite materials are especially suitable for large or massive implants and the like medical devices, such as plates, nails or screws, or to any other implants and medical devices exposed to compression, tension and/or torsion forces. Such nails or screws may have a length of the least 10 cm, at least 15 cm or at least 20 cm. The materials can provide desired mechanical properties to such products, such as bending strength, torsion strength, impact strength, compressive strength and tensile strength.

In one embodiment the bioresorbable implant comprises or is an intramedullary nail. Intramedullary nail, also called as intramedullary device, intramedullary rod or inter-locking nail, is conventionally a metal rod which is designed to be forced into the medullary cavity of a bone, especially to treat fractures of long bones of the body. The present hybrid composite materials are especially suitable for preparing intramedullary nails, which are large structures usually made of titanium which therefore needs removing from a body. This may be a laborious and high-risk operation requiring anaesthesia, surgical methods and use of force, which may lead to complications, further injuries or other non-desired effects such as discussed herein. With the present hybrid materials it is possible to provide biodegradable intramedullary nails, which do not need removing but which exhibit very good mechanical properties required in such large nails, such as high strength, stiffness and modulus. With the present manufacturing methods it is possible to easily obtain such massive nails with desired size and properties. As the product is biodegradable, it does not require removing so many of the drawbacks of the conventional intramedullary nails can be avoided.

Figure 3:
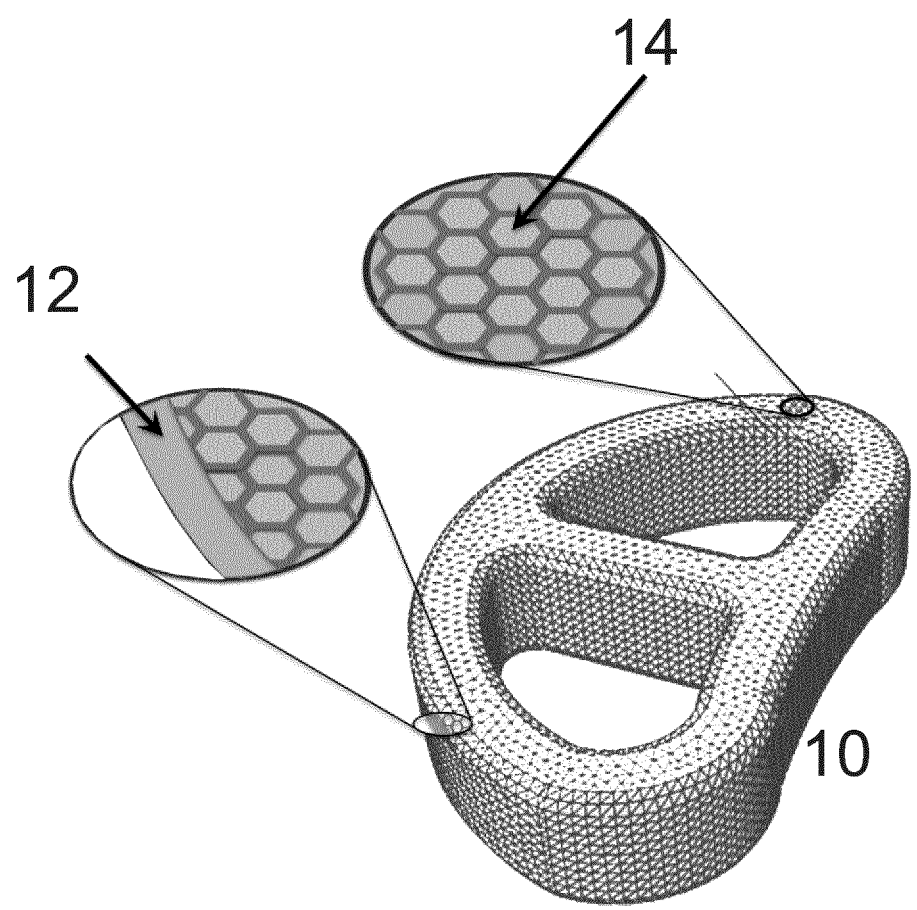
FIG. 3 shows an example of a spinal cage with a honeycomb structure

In one embodiment the bioresorbable implant comprises or is a scaffold or a cage, such as spinal cage. A spinal cage, also called as an interbody cage or interbody fusion cage, is a prosthesis used in spinal fusion procedures to maintain foraminal height and decompression. They may be for example cylindrical or square-shaped, and may be threaded. Such implants are inserted when the space between the spinal discs is distracted, such that the implant, when threaded, is compressed like a screw. FIG. 3 shows an example of a spinal cage 10 comprising a magnesium alloy honeycomb structure 14, which may be filled with osteoconductive or osteoinductive material, such as polymer composite material. The outside layer 12 is formed of glass-fiber-polymer layer surrounding and supporting the magnesium alloy structure. As the spinal cage 10 is open including two large apertures and honeycomb structure and is subjected to compressing forces during use, it is important that the whole structure can tolerate these mechanical forces without deforming. In general, the present hybrid materials are suitable for supporting different kind of cellular or porous structures, such as said honeycomb structures or other structures containing pores, voids or apertures. The present materials may comprise such cellular portions or other porous portions, such as cellular portions comprising or consisting of magnesium or magnesium alloy. Examples of such products include the cages, scaffolds or other applicable products disclosed herein.

The present hybrid composite materials are especially suitable for such scaffolds and cages, which must tolerate high pressure load or stress. Conventional biodegradable materials are not very durable in such use, especially polymer-based materials tend to compression creep and flatten. In the present hybrid materials the non-creeping glass fiber can hold the implants together, and the magnesium provides compression strength. The glass fiber may be wound or otherwise placed around the reinforcing form of magnesium or magnesium alloy, so the spreading of the magnesium material can be suppressed.

The basic premise of a spinal fusion is the creation of a bone "bridge" that connects strong and healthy bone above the weakened spinal segment with strong and healthy bone below it.

Long-term spinal stability is best achieved with good fusion of the bones. The process of bone fusion takes several months or up to a year or more for patients with fusions that extend over several spinal segments. Current metallic cages e.g. titanium cages, which are currently the golden standard in spinal fusion, are often associated with excessive rigidity that may increase postoperative complications such as stress shielding, device-related osteopenia, and subsidence. Although superior in mechanical strength, metallic cages are non-bioactive and often fail to effectively transfer loads to stimulate bony tissue remodeling. Radiopaque metallic cages also interfere with visualization of bony fusion at the graft site during postoperative follow-up, making it difficult to determine the progress of bony healing. The present biodegradable cages are especially suitable in spinal procedures involving interbody fusion to resolve complications associated with the use of nondegradable cages, such as stress shielding and long-term foreign body reaction. In prior art the relatively weak initial material strength and low creep resistance of biodegradable cages compared to permanent materials and subsequent decrease of strength due to degradation has been problematic and has not yielded favourable clinical outcome. The bioactivity of the present biodegradable hybrid composite enables fast bone-bonding of the cage to vertebrae and prevents implant migration and displacement, and moreover stimulates bony tissue remodeling over and through the hybrid composite implant from vertebra to vertebra i.e. spinal fusion. The mechanical properties of hybrid composite cage are isoelastic with cortical bone as shown in example 6 and not causing stress shielding but stronger than current biopolymer cages and therefore enable adequate stability to spinal fusion. Additionally the hybrid composites are MRI safe and they do not interfere with post-operative visualization.

In one embodiment the implant comprises or is a screw. The screw may be a trauma screw or orthopaedic surgical screw. A screw usually includes one or more screw thread(s).

Kirschner wire, also called as K-wire or K-pin, is a sharpened, smooth wire or pin. They may be provided in different sizes and are used to hold bone fragments together (pin fixation) or to provide an anchor for skeletal traction.

The hybrid composite material may also be used as a porous tissue engineering scaffold. The scaffold, or the composite material or a medical device containing thereof, may have a porosity degree in the range of 40-95%, such as in the range of 40-60% 40-90% 60-90% or 60-80%, preferably at least 80%, and more preferably at least 90%.

The advantage of medical devices according to the present application is that they disappear from the body by degradation without giving rise to adverse events such as too fast hydrogen evolution.

Depending on the application and purpose of the medical device material, the medical devices, in addition to being biocompatible, also exhibit controlled resorption in the mammalian body. The optimal resorption rate is directly proportional to the renewal rate of the tissue in the desired implantation location. In the case of bone tissue, a considerable proportion of the implant is preferably resorbed/decomposed within 12 to 24 months in the tissue. In cases where more physical support to the healing tissues is desirable, the resorption rate might be several months or even several years. Furthermore, the invention can be made use of in medical devices such as cannulas, catheters and stents.

Another advantage of the medical devices or a structural part is their strength and feasible manufacturing. Medical device or structural part can be manufactured by arranging any reinforcing form of magnesium or magnesium alloy and bioresorbable glass fibers in a bioresorbable polymer matrix and using one or more of suitable of polymer or composite processing device(s) or equipment, such as a mechanical processing device, for example an open or closed batch mixer or kneader, extruder including coextrusion and thermoplastic pultrusion, injection molding machine including insert molding, reactive injection molding (RIM), lamination, calenders, transfer molding, compression molding, mechanical machining, pultrusion, solvent casting, 3D printing, filament winding, automated tape lay-up, automated fiber placement or other standard melt processing or melt mixing equipment known in the field and including combinations of aforementioned, producing and/or shaping into an implant or structural part having a desired orientation and ratio of the magnesium or magnesium alloys and continuous bioresorbable glass fibers and/or chopped/cut fibers and/or woven, nonwoven mats/textiles.

The medical devices, such as the implants, may be used in medical treatment methods, such as methods comprising inserting the medical device into a subject, such as a patient. For example, such a method may comprise
  preferably recognizing a subject in need of treatment or therapy,
  providing the medical device,
  inserting the medical device into the subject.

The subject may be human or animal subject. The need of therapy may be caused by a damage in a bone or other suitable tissue. For example the subject may suffer from a bone fracture or other damage, or other applicable condition, such as ones disclosed herein.

The present application provides a method for preparing or manufacturing a medical device or a part thereof, the method comprising
  providing a reinforcing form of magnesium or magnesium alloy and bioresorbable glass fibers in a bioresorbable polymer matrix in form or to form composite material,
  providing one or more processing device,
  processing the composite material with the processing device into a medical device or a part thereof.

The method may comprise first providing magnesium, preferably in a suitable form, providing bioresorbable glass fibers in a bioresorbable polymer matrix, and combining these to form the composite material. A processing device, which may be the same, similar or different as in the subsequent step, may be also used for processing the bioresorbable glass fibers in a bioresorbable polymer matrix.

The formed composite material may be any type of applicable composite material described herein. The process for manufacturing the hybrid composite material may be a continuous process or a batch process.

In order to modify the degradation of the final implants, to enhance their surface properties, or to add biologically active compounds therein, they can be further modified by an additional resorbable polymer coating layer with a process that may include co-extrusion, dip coating, electro spraying, injection molding, solution impregnation or any other known technique used in polymer, pharmaceutical, device or textile industry. The polymers may be those mentioned below.

Hybrid composite serves also as a solution for current problems in the technical field where environmental control and pollution prevention requires sustainable solution with fully degradable material which can be used in structural parts and degraded after life cycle of the product without leaving any harmful and toxic by-products left in the nature.

A hybrid composite can be used for primary structures in commercial, automotive, industrial, aerospace, marine, and recreational structures or objects. It has a wide array of benefits in the aerospace industry, such as great fatigue and corrosion resistance, and excellent impact resistance. The most significant advantage is weight reduction, where it could generate savings in the range of 20%-50% compared to traditional metal parts. Furthermore, the mechanical properties can be tailored by "lay-up" design, with tapering thicknesses of reinforcing layers and changing orientations.

Magnesium and Magnesium Alloys

Magnesium is very attractive material as it has the combination of relatively good strength, low weight and good surface quality. In structural applications, where weight plays a major role, magnesium is a good choice. Its recyclability property also gives an edge. The use of magnesium and its alloys in automotive components was limited in the early sixties and seventies but today the awareness on fuel savings and environmental protection through reduced $CO_2$ emissions makes this material attractive. Magnesium is considered to be a good choice material in the areas of defense and aerospace engineering for aircraft and missile components, aircraft engine mounts, control hinges, fuel tanks, wings. In automotive sector magnesium is used for wheels, housings, transmission cases, engine blocks, steering wheels and columns, seat frames, electronic goods like laptops, televisions, cell phones and in many more areas.

Magnesium is found to be the 8th most-abundant element in the earth's crust by mass, 9th abundant element in the universe as a whole. It occupies the 4th position among the elements that contribute earth mass as a whole followed by iron, oxygen and silicon. It is ranked 3rd most-abundant element dissolved in seawater. Magnesium is also needed by the human body as a mineral. Magnesium is the second most abundant, intracellular, divalent cation in human body. Magnesium and its corrosion products exhibit high biocompatibility. It has a structural role in the cell membrane and in chromosomes, and is involved in various mechanisms, e.g. as a cofactor for over 300 enzymes and in metabolic pathways. Bone contains approximately 67% of the body's magnesium, 30% of this being exchangeable due to its presence on the surface of bone, thus providing a dynamic store for the maintenance of magnesium homeostasis. On the other hand, body can easily and effectively get rid of excess magnesium through kidneys.

The magnesium and magnesium alloys are used as one reinforcing component in the hybrid composite. Magnesium can be used as a pure. The definition of pure means in this context that magnesium having less than 0.1 wt. % of one or more other elements with the remainder being magnesium. Preferably pure magnesium has less than 0.01 wt. % of one or more other elements with the remainder being magnesium and most preferably less than 0.005 wt. %.

Magnesium is considered biocompatible, bioresorbable and non-toxic and has been shown to increase the rate of bone formation i.e. to be osteoinductive, because magnesium is also an important ion in the formation of the biological apatite's that make up the bulk of bone mineral, a key part to new bone formation. therefore, magnesium can be classified as bioactive material. Magnesium is also known to have a positive influence on bone fragility and strength.

Pure magnesium is incapable of providing the necessary mechanical strength and corrosion properties required for a wide variety of implant applications, but the hybrid composites disclosed herein make it possible to use also pure magnesium, since the main input from magnesium or its alloys comes from stiffness and flexural modulus. The bioresorbable glass fiber reinforced matrix upregulates the strength, corrosion properties and hydrogen gas evolution. The release of hydrogen gas and subsequent cyst formation following implantation of magnesium or magnesium alloys can cause various problems. Gas pockets may form next to the implant that cause separation of tissue and/or tissue layers. Hydrogen gas bubbles may delay healing at the surgical site, leading to necrosis of surrounding tissue. In the worst-case scenario, gas bubbles could block the blood stream, causing death. If the degradation is too rapid, the amount of hydrogen gas produced will accumulate where it cannot diffuse through the surrounding soft tissues at a sufficient rate. If even higher mechanical strength or different resorption rate is required magnesium alloys can be used, magnesium alloys are mixtures of magnesium with other metals, but potential alloying elements need to be carefully considered. Since magnesium and its alloys are extremely susceptible to galvanic corrosion, which can cause severe pitting in the metal resulting in decreased mechanical stability and an unattractive appearance. Corrosion can be minimized using high purity alloys that maintain heavy metal impurities and iron, nickel and copper below a threshold value. The development of suitable biodegradable implant alloys is therefore a multidisciplinary challenge, since freedom in alloy design must be confined to a range of alloying additions that are biologically non-toxic while still providing the requisite mechanical properties. This leaves a small number of compatible elements that can provide mechanical or corrosion benefits when alloyed with Mg. This is in addition to the potential harm of hydrogen evolution and soluble (or insoluble) corrosion products, which may contain elements of unknown toxicity. Common alloying elements for magnesium include aluminum, zinc, calcium, rare-earth elements, lithium, manganese, silicon and zirconium. A rare-earth element (REE) or rare-earth metal (REM), as defined by the International Union of Pure and Applied Chemistry, is one of a set of seventeen chemical elements in the periodic table, specifically the fifteen lanthanides, as well as scandium and yttrium. Of all the available elements, perhaps the most controversial is aluminum and REE's in medical field. Aluminum and REE's are the most common alloying addition to structural magnesium alloys, allowing a gain in mechanical properties while not increasing the corrosion rate, but biocompatibility concerns exist for alloys containing REE's or aluminum, which, although studied in vitro and in vivo, also suffer from a lack of knowledge of their long-term effects when implanted. This creates the potential that the significant amount of work that has been and will be performed using alloys containing Aluminum or REE's may, in the end, go unused if the materials cannot be proven to be non-toxic.

The rapid degradation of magnesium alloys may cause an adverse biological response as magnesium and other element ions are released too quickly into the surrounding tissues. All the alloying elements will eventually enter the patient and must be selected with non-toxicity as a primary factor. One approach is to use elements which normally present in the body e.g. zinc, calcium, silicon and manganese.

ASTM (American Society for Testing and Materials) specification B275 names the magnesium alloys with two letters defining the elements, with numbers denoting the percentage and an additional digit to indicate intermediate properties. For example, AZ 91 Mg alloy contain aluminum (Al) and zinc (Zn) in 9%, 1% respectively in total and the rest by pure magnesium. Table 1 lists as example various alloying elements that can be added to magnesium to improve the properties.

TABLE 1

| Alloying element | Properties | Effect |
| --- | --- | --- |
| Aluminum | Hardness | increases |
|  | Strength | increases |
|  | Ductility | decreases |
| Beryllium | Oxidation | decreases |
| Calcium | Oxidation | decreases |
| Cerium | Corrosion resistance | increases |
|  | Yield strength | decreases |
| Copper | Strength | increases |
|  | Ductility | decreases |
| Nickel | Yield an ultimate strength | increases |
|  | Ductility | decreases |
|  | Corrosion resistance | decreases |
| Rare-earth elements | High temperature creep | increases |
|  | Corrosion resistance | increases |
|  | Strength | increases |
| Silicon | Corrosion resistance | increases |
| Zinc | Corrosion resistance | increases |

Any magnesium alloying system can be used in hybrid composite, but when hybrid composite is used as medical device, then any biocompatible magnesium alloying system can be used. The preferable alloying elements are zinc, calcium, manganese, silicon, zirconium, aluminum, lithium, rare-earth elements and mixture of those. The most preferable alloying elements are silicon, zinc and calcium.

Magnesium or magnesium alloy is a reinforcement, and may be in a form of a rod, a plate, a core, a tube or fibers or other reinforcing shape, which may be a physical form which brings a reinforcing effect to the hybrid composite and may be embedded by bioresorbable fiber reinforced polymer matrix.

According to examples, the amount of the other metals in a magnesium alloy, or in magnesium alloying system, may be 0.1-49 weight-%, preferably 0.25-10 weight-%, and most preferably 0.5-2 weight-% of the total weight of the magnesium alloy material.

According to examples, the amount of the magnesium or the magnesium alloy in the hybrid composite may be 1-99 weight-%, preferably 10-90 weight-%, more preferably 20-80 weight-%, and most preferably 30-70 weight-% of the total weight of the hybrid composite material.

Although the lower strength of Mg compared to Ti may be beneficial with respect to stress shielding, it also means that there may be a greater chance of failure in high load applications, such as the spine where compressive loads during certain activities may exceed 3500 N. It is vital to ensure that any implant is designed to sustain its load without deformation. However, this aspect is even more crucial when considering degradable materials, as an appropriate mechanical support is required throughout the entire bioresorption and bone remodeling process Chemical Coating As explained in previous, magnesium and its alloys have good physical and mechanical properties for a number of applications. In particular, its high strength to weight ratio makes it an option for automotive and aerospace applications, where weight reduction is of significant concern. Unfortunately, magnesium and its alloys are highly susceptible to corrosion, particularly in water/moist or salt-spray conditions. This has limited its use in the automotive, aerospace and medical industries, where exposure to harsh service conditions is unavoidable. The simplest way to avoid corrosion is to coat or surface treat the magnesium-based substrate to prevent contact with the environment. However, chemical coatings are just a few micrometers thick and thus they are only offering a limited protection. However, they are excellent primers for a subsequent organic coating in hybrid composite if a good adhesion is required for between metal and bioresorbable glass fiber reinforced polymer matrix. Moreover, the chemical coating may also improve the corrosion resistance properties and even hinder the hydrogen gas evolution on top of the bioresorbable glass fiber reinforced polymer matrix.

In order a coating to provide adequate corrosion protection, the coating must be uniform, well adhered, pore-free and possibly self-healing for manufacturing methods of hybrid composite where physical damage to the coating may occur. One of the problems with magnesium is its chemical reactivity. As soon as it comes in contact with air or water an oxide/hydroxide layer forms on the surface which can have a detrimental effect on coating adhesion and uniformity.

Applied coating/coatings could be also partial on purpose. The coating/coatings may have a certain pattern or the variable thickness (thickness gradient), which provides a design specifically optimized and/or programmed, i.e. pre-defined, corrosion rate or adhesion behavior i.e. for example the mechanical properties of the material may be arranged to start to deteriorate in a controlled way by losing the adhesion or by corrosion first from the programmed location.

There are a number of possible coating technologies available for magnesium and its alloys, each with their own advantages and disadvantages. These include electrochemical plating, conversion coatings, anodizing, hydride coatings, ceramic coatings and vapor-phase processes.

The primary purpose of optional chemical coating in the present case is to provide chemical or physical adhesion from magnesium or magnesium alloy to bioresorbable polymers and secondary corrosion resistance to magnesium or magnesium alloy and tertiary other properties e.g. antimicrobial or antibacterial properties.

Therefore in one embodiment the magnesium or the magnesium alloy is coated, either fully or partially, preferably with one or more substances disclosed herein and/or by using any of the methods disclosed herein.

Examples of substances which can be used for coating, but are not limited to, include organo-silanes, organo-titanates, organo-zirkonates, functionalized biodegradable polymers with capability to react with surface treated or untreated magnesium or its alloys, aluminum oxide, zinc oxide, metals e.g. zinc, gold, silver, copper, and nickel.

The chemical coating is optional and the chemical coating may comprise one or more layers of one or more substances in one layer or in different layers.

Electrochemical Plating

The plating process can be subdivided into two types: electroplating and electroless plating. In both cases a metal salt in solution is reduced to its metallic form on the surface of the workpiece. In electroplating the electrons for reduction are supplied from an external source. In electroless or chemical plating the reducing electrons are supplied by a chemical reducing agent in solution or, in the case of immersion plating, the substrate itself. Cu—Ni—Cr plating on magnesium or its alloys have been shown to have good corrosion resistance in interior and mild exterior environments. as magnesium and its alloys are also prone to galvanic corrosion because most other metals have a more noble electrochemical potential. Electrolytic contact with another metal can cause the formation of local corrosion cells on the surface leading to pitting. Therefore, the metal coating must be pore free otherwise the corrosion rate will increase. A minimum coating thickness of 50 µm has been suggested to ensure pore-free coatings. Another advantage of electroless plating is that second phase particles such as carbides, diamonds or PTFE can be co-deposited during the plating process to improve the hardness, abrasive properties or lubricity of the bioresorbable glass fiber reinforced polymer matrix. To date zinc, gold, silver, copper, and nickel have been directly plated onto magnesium, and are used as under coatings or primer for subsequent process steps. Especially, zinc, silver and copper bring also antimicrobial properties to the chemical coating layer.

Conversion Coatings

Conversion coatings are produced by chemical or electrochemical treatment of a metal surface to produce a superficial layer of substrate metal oxides, chromates, phosphates, silanes, titanates, zirconates or other compounds that are chemically bonded to the surface. Conversion coatings provide an adhesion by chemical bonding and/or affinity or physical entanglements polymer matrix and protect the substrate from corrosion by acting as an insulating barrier of low solubility between the metal surface and the environment and/or by containing corrosion inhibiting compounds. The use of alkoxy organo-silanes, organo-titanates, organo-zirconates i.e., those containing primary, secondary or tertiary alkoxy groups directly attached to silicon, titanium, zirconium as coupling agents for particulate material and polymeric resins is well known. Also use of fluorotitanates and zirconates are well known in coating of magnesium and magnesium alloys. Another chemical conversion process is to use a solution containing an organic additive and an organic acid, which has been shown to increase adhesion to polymers and passivate the metal surface. In such a process, after degreasing, the magnesium or its alloy is immersed in a solution containing sodium benzoate, sodium gluco-sate and an organic acid. The coatings produced were shown to have slightly better corrosion resistance than a chromate treated sample and environmentally and toxically safe. The morphology of the conversion coatings provides a good base for subsequent process steps which can further improve the adhesion and corrosion resistance of the treated magnesium part. In an alternative chemical coating process is a chemical treatment involving acid pickling in a hydroxy acetic acid solution followed by conversion coating with an organo functional silane compound. This process has been shown to maintain good adhesion and corrosion resistance in salt spray tests for coatings on magnesium alloys.

Hydride Coating

A technique for producing a magnesium hydride coating on magnesium and its alloys by electrochemical means has been developed as an alternative to Cr-based conversion coatings.

Anodizing

Anodizing is an electrolytic process for producing a thick, stable oxide film on metals and alloys. These coating layers may be used to improve polymer adhesion to the metal, as a key for dyeing or as a passivation treatment. The coatings have a thin barrier layer at the metal-coating interface followed by a layer that has a cellular structure. Each cell contains a pore whose size is determined by the type of electrolyte and its concentration, temperature, current density and applied voltage. Their size and density determine the extent and quality of sealing of the anodized coating.

Magoxid-coat process is an anodic plasma-chemical surface treatment that forms an oxide ceramic layer on magnesium materials. The plasma is discharged by an external power source in a slightly alkaline electrolyte near the surface of the workpiece, which acts as the anode of the system. The oxygen plasma generated causes partial short-term surface melting and ultimately the formation of an oxide-ceramic layer. The anodizing bath for this process is free of chloride and may contain inorganic anions such as phosphate, borate, silicate, aluminate or fluoride. The bath may also contain organic acids such as citrate, oxalate and acetate. A source of cations is also present and may be chosen from alkali ions, alkaline earth ions or aluminum ions. Finally, a stabilizer such as urea, hexamethylenediamine, hemethylenetetramine, glycol or glycerin is also added. The coating consists of three layers, a thin (about 100 nm) barrier layer at the metal surface followed by a low porosity oxide ceramic layer and finally a higher porosity ceramic layer. The final layer acts as a good base for polymer adhesion and impregnation treatments. Impregnation of the coating with particles of fluorine polymers has been shown to significantly improve the load bearing properties of the coatings while maintaining good adhesion and corrosion resistance. The coating has been shown to consist of mainly $MgAl_2O_4$. This process is capable of producing uniform coatings even on edges and cavities.

Gas-Phase Deposition Processes

All the processes discussed thus far have been wet chemical surface treatments. Adhesive and protective coatings can also be produced from the gas phase. These are typically metallic or metal oxide coatings but can include organic coatings such as thermal spray polymer coatings and diamond like coatings. Thermal spray coatings are gas-phase deposition processes where the coating material, which can be metal, ceramic, cermet or polymeric is fed to a torch or gun where it is heated to above or near its melting point. The resulting droplets are accelerated in a gas stream onto the substrate and the droplets flow into thin lamellar particles and adhere to the surface. A number of coating techniques fall under this umbrella including flame spraying, wire spraying, detonation gun deposition, plasma spray and high velocity oxyfuel. Some of the advantages of this technique include the ability to create a coating of virtually any material that melts without decomposing, minimal substrate heating during deposition and the ability to strip and recoat worn or damaged coatings without changing the properties or dimensions of the part. As with most surface treatments, in order to ensure adequate adhesion, the substrate must be properly prepared. The substrate must be both cleaned and roughened prior to the application of the thermal spray coating. Chemical vapor deposition (CVD) is a vacuum deposition method used to produce high quality, high-performance, solid materials. The process is often used to produce thin films. CVD to deposit materials in various forms, including: mono-crystalline, polycrystalline, amorphous, and epitaxial. These materials include: silicon (dioxide, carbide, nitride, oxynitride), carbon (fiber, nanofibers, nanotubes, diamond and graphene), fluorocarbons, filaments, tungsten, titanium nitride. Chemical vapor deposition (CVD) can be defined as the deposition of a solid on a heated surface via a chemical reaction from the gas phase. Advantages of this technique include deposition of refractory materials well below their melting points, achievement of near theoretical density, control over grain size and orientation, processing at atmospheric pressure and good adhesion. This process is not restricted to line of sight like most physical vapor deposition (PVD) processes so deep recesses, high aspect ratio holes and complex shapes can be coated. A plasma-assisted CVD technique has been successfully used to deposit TiCN and ZrCN layers on magnesium alloys. A patented process for producing a protective film on magnesium containing substrates has been disclosed [U.S. Pat. No. 4,980,203]. The coating process involves CVD of an intermediate aluminum layer, followed by a metallic oxide layer of titanium oxide, aluminum oxide, zirconium oxide, chromium oxide or silicon oxide. Diamond like carbon films can be produced using a number of different processes such as PVD, CVD and ion implantation. Diamond-like carbon films on magnesium alloys with good lubricity, corrosion resistance, adhesion and smoothness have been produced using a CVD process. PVD involves the deposition of atoms or molecules from the vapor phase onto a substrate. This process includes vacuum deposition, sputter deposition, ion plating, pulsed-laser deposition and diffusion coatings. In a patented process [JP2025564] PVD-PLD has been used to coat magnesium substrates with titanium or titanium alloy material. A focused laser beam is used to heat and vaporize the titanium or titanium alloy target. The vapor is deposited on the magnesium or magnesium alloy substrate to form a thin film.

Atomic layer deposition (ALD) is a thin-film deposition technique based on the sequential use of a gas phase chemical process; it is a subclass of chemical vapor deposition. The majority of ALD reactions use two chemicals called precursors. These precursors react with the surface of a material one at a time in a sequential, self-limiting, manner. Through the repeated exposure to separate precursors, a thin film is slowly deposited. ALD is good method to produce thin coatings based on metal oxides (e.g. $Al_2O_3$ and ZnO) and nitrates (e.g. SiN).

Organic finishing is typically used in the final stages of a coating process. These coatings can be applied to enhance adhesion, corrosion resistance, abrasion and wear properties. An appropriate pretreatment process is required in order to produce coatings with superior adhesion, corrosion resistance and appearance. Magnesium surfaces must be free of surface contamination, smut and loose silicates, oxides and intermetallic compounds. Cleaning processes for magnesium can involve mechanical pretreatment, solvent cleaning or alkaline cleaning. Cleaning is typically followed by a pickling or an etching step coupled with a chemical treatment, such as conversion coating or anodizing. These treatments roughen and chemically modify the surface so that the organic coating will have good adhesion to the surface. Another technique for treating magnesium surfaces prior to the application of an organic coating involves exposing the material to an aqueous solution containing an organic compound after appropriate cleaning and pickling procedures. The compound must have a particular structure XYZ, where X and Z are both polar functional groups and Y is a straight chain structure with 2-50 carbon atoms. Some examples of these include 1-phosphonic acid-12-(N-ethylamino)dodecane, I-phosphonic acid-12-hydroxy-dodecane, p-xylylene diphosphonic acid and 1,12-dodecane diphosphonic acid. These compounds react with the hydroxide groups on the magnesium surface through the acid groups to form a chemical bond. There is also a reaction between the remaining functional groups and the subsequent organic coating. These coatings are to significantly improve polymer adhesion and to inhibit corrosion. Organic coating systems can include a variety of different processes that make use of biodegradable organic polymers, such as painting, powder coating, E-coating (cathodic epoxy electrocoating) and the application of lacquers, enamels and varnishes. Powder coatings can be applied in a number of ways including electrostatic powder spraying, fluidized bed or flame spraying of thermoplastic powders. Flame spraying has been used in the application of ethylene acrylic acid (EAA) copolymers on a variety of substrates. In this process the plastic powder is propelled through a flame that heats and melts the polymer and the surface so that the coating particles coalesce and flow into a continuous coating. The EAA polymers have been shown to have excellent adhesion to metals due to the acrylic acid functional groups, which promote adhesion by hydrogen and ionomeric bonding to the substrate. These systems can be based on a variety of biodegradable or water soluble coating resins such as polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/e-caprolactone copolymers, L-lactide/DL-lactide copolymers, glycollide/L-lactide copolymers (PGA/PLLA), polylactide-co-glycolide; terpolymers of PLA, such as lactide/glycolide/trimethylene carbonate terpolymers, lactide/glycollide/e-caprolactone terpolymers, PLA/polyethylene oxide copolymers; polydepsipeptides; unsymmetrically 3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-s-capralactone, Polytyrosines and its copoly mers; polyacrylam ides, poly(e-caprolactone-DL-lactide) copolymers; methylmethacrylate-N-vinylpyrrolidone copolymers; Polyvinylpyrrolidone and its copolymers; polyesteramides; polyacrylic acids, polybutylene succinate, polyoxazolines, Polyethylene glygols, polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanoic acids; polycarbonates; polyorthoesters; polyphosphates; Polyphosphazenes; poly(ester anhydrides); biodegradable liquid crystal polymers; Xanthan Gum; Pectins; Dextran; Carrageenan; Guar Gum, Cellulose Ethers; Glucomannan; Sodium CMC; HPC; HPMC; and mixtures thereof; and natural polymers, such as sugars; Starch or Starch Based Derivatives, cellulose and cellulose derivatives, polysaccharides, collagen, chitin, chitosan, fibrin, hyaluronic acid, polypeptides and proteins. Mixtures and copolymers of any of the above-mentioned polymers and their various forms may also be used. Traditionally, organic coatings have been solvent based which poses a significant environmental concern with their use. However alternative processes that eliminate this problem are available. Some of these include powder coatings, the use of compliance solvents and waterborne solvents. The primary function of organic coatings is to act as an interface between the metal substrate and polymer matrix. It is important that these coatings provide functional groups and/or chemical affinity and/or physical entanglements to react to form a chemical bond or physical bond with polymer matrix. In manufacturing methods where physical damage is likely to occur it is also important that the coating have self-healing characteristics. This can be accomplished by the presence of corrosion inhibiting pigments or additives in the coating or using a sacrificial anodic compound in the coating. For an organic coating to act as an effective adhesive and protection, it must be uniform and well-adhered to the magnesium or magnesium alloy or primer. a multiple layer coating system may be used which is consisting of a topcoat, that is typically the most hydrophobic and UV resistant coating, and primer and mid-coats that have high crosslink density and wet adhesion to the magnesium and each other. With a multiple layer system, it is unlikely that defect areas will overlap, this ensures that the substrate is completely coated with organic material. These coatings may be also elastomeric to absorb and dissipate impact energy. The organic coating may also include additives e.g. an antimicrobial agent such as halogen substituted silanes.

Sol-Gel Process

Synthesis of gels or glasses by the sol-gel process involves the hydrolysis and condensation polymerization of metal alkoxides, alkoxy-silanes, -titanates, -zirconates and/or phosphates. This process can be used to produce polymeric networks of inorganic-organic composite materials. It is possible to form adherent, uniform coatings on metal surfaces by the addition of components, to the reaction mixture, that are reactive with the surface that is to be coated. This process can produce corrosion-protective coatings on magnesium and magnesium alloys by a simple wet coating technique through the formation of a stable tailored interface. The coatings are transparent with excellent adhesion, scratch and abrasion resistance, and corrosion protection. One approach is to produce bioglass coating to the magnesium and its alloys by Sol-gel process, one example of such a sol-gel bioglass composition is 58S (60 mol % $SiO_2$, 36 mol % CaO, 4 mol % $P_2O_5$).

Coatings for biomaterials, especially bioresorbable magnesium and its alloys, have the same requirements as the base materials themselves of being biocompatible and fully degradable. The latter point is particularly salient for understanding what occurs over the implant life cycle. In the case of magnesium, coatings themselves cannot be perfect barriers to corrosion (which would be the goal of a coating system on a structural non-degradable material). To allow an hybrid composite implant to biodegrade, the coatings must, at some stage, cease to be a adhesion interface and corrosion barrier, although they are required to provide an effective method to provide good adhesive interface to polymer and reduce the initial corrosion rate of the bare metal so the surrounding bone tissue (in the case of orthopedics) may start to form. Ideally, the coating would itself degrade gradually, helping to control the overall corrosion process while leaving no harmful traces. The chemical coatings must be biocompatible and non-toxic and display a controlled biodegradation rate.

One example uses chemical coating in magnesium and magnesium alloys to provide chemical or physical adhesion from magnesium or magnesium alloy to bioresorbable polymers.

One example uses chemical coating in magnesium and magnesium alloys to provide corrosion resistance to magnesium or magnesium alloy.

One example uses chemical coating in magnesium and magnesium alloys to provide other properties e.g. antimicrobial or antibacterial properties to the interface.

The thickness of chemical coating may be from a molecular layer to several hundreds of micrometers and chemical coating may consist of or comprise one layer or several layers of one or more different substances.

Bioresorbable Glass Fiber Reinforced Polymer Matrix

The present application provides a hybrid composite material comprising magnesium or magnesium alloy included, such as embedded, in a discontinuous or continuous bioresorbable glass fiber reinforced polymer matrix. The composite material disclosed herein preferably comprises free fiber orientation in a one or more successive layers, preferably at least glass fibers, wherein the layer comprises a bioresorbable polymer matrix and a bioresorbable reinforcing fiber or fiber bundle.

The term "free fiber orientation" refers to unrestricted choice of fiber orientation of the bioresorbable reinforcing fiber or fiber bundle of the bioresorbable glass fiber reinforced polymer matrix when designing the desired fiber orientation of the orthopedic implant. The desired fiber orientation, however, may be dependent of the requirements of the application.

The bioresorbable glass fiber may be used as continuous form as strands, roving's, yarns, tapes, textiles or chopped to form chopped strand segments. The chopped strand segments may be compounded with a polymeric resin during an extrusion process and the resulting short fiber, compounded pellets or granules. On the other hand, the continuous fiber strand packages may be used in continuous fiber thermoplastic composite fabrication using a long fiber thermoplastic (LFT) process to form continuous glass fiber reinforced polymer strands, rods, tapes, textiles or chopped long fiber reinforced pellets or granules. These forms or structures, in turn, may be used to form hybrid composite articles. Pellets or granules may be added, and they may be compressed or compression molded to provide desired surface, such as rough surface, and/or to fill any pores or other apertures of voids in the magnesium or magnesium alloy, which may therefore have a cellular structure.

In an embodiment of the hybrid composite, a continuous glass fiber reinforced polymer matrix is used with magnesium or magnesium alloy comprising a bioresorbable polymer matrix and continuous bioresorbable reinforcing glass fiber, wherein the glass fiber has a tensile strength of about or over 2000 MPa. This enables obtaining a hybrid composite tensile strength of more than 450 MPa, and a composite flexural strength of more than 450 MPa. Thereby an orthopedic implant having composite tensile strength of more than 450 MPa, and a composite flexural strength of more than 450 MPa, is obtained.

The term "bioresorbable glass fiber reinforced polymer matrix" refers to any suitable depositable structure comprising the bioresorbable polymer matrix and the bioresorbable reinforcing fiber or fiber bundle in the structure. The bioresorbable reinforcing fiber may be discontinuous or continuous or mixture of those in the structure.

The weight ratio of the continuous bioresorbable reinforcing fiber or fiber bundle to the bioresorbable polymer is preferably such that the bioresorbable reinforcing fiber content is 1 to 99 weight % of the total weight of the bioresorbable glass fiber reinforced polymer matrix, preferably 20 to 80 wt %, more preferably from 30 to 70 wt % and most preferably 40 to 60 wt %.

The smallest dimension of the bioresorbable glass fiber reinforced polymer matrix is preferably from 0.05 mm to 100 mm, more preferably 0.1 mm to 20 mm, even more preferably from 0.5 mm to 10.0 mm, most preferably from 0.8 mm to 5.0 mm. The bioresorbable polymer may be a homopolymer or a copolymer, including random copolymer, block copolymer, or graft copolymer. Further, the bioresorbable polymer may be a linear polymer, a branched polymer, or a dendrimer. The bioresorbable polymers may be of natural or synthetic origin.

One or more of the following resorbable polymers, copolymers and terpolymers may be used as suitable bioresorbable polymers. For example, polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/e-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/e-caprolactone terpolymers, PLA/polyethylene oxide copolymers; polydepsipeptides; unsymmetrically 3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-s-capralactone, Polytyrosines and its copolymers; polyacrylam ides, poly(e-caprolactone-DL-lactide) copolymers; methylmethacrylate-N-vinylpyrrolidone copolymers; Polyvinylpyrrolidone and its copolymers; polyesteramides; polyacrylic acids, polybutylene succinate and its copolymers; polyoxazolines, Polyethylene glygols, polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanoic acids; polycarbonates; polyorthoesters; polyphosphates; Polyphosphazenes; poly(ester anhydrides); biodegradable liquid crystal polymers; Xanthan Gum; Pectins; Dextran; Carrageenan; Guar Gum, Cellulose Ethers; Glucomannan; Sodium CMC; HPC; HPMC; and mixtures thereof; and natural polymers, such as sugars; Starch or Starch Based Derivatives, cellulose and cellulose derivatives, polysaccharides, collagen, chitin, chitosan, fibrin, hyalyronic acid, polypeptides and proteins. Mixtures and copolymers of any of the above-mentioned polymers and their various forms may also be used.

Particular examples of suitable bioresorbable polymers include, but are not limited to, polymers made from, obtained from or comprising, lactide, glycolide, caprolactone, valerolactone, carbonates, dioxanones, 6-valerolactone, ethylene glycol, ethylene oxide, esteramides, y-hydroxyvalerate, B-hydroxypropionate, alpha-hydroxyacid, hydroxybuterates, polyorthoesters, hydroxy alkanoates, tyrosine carbonates, polyimide carbonates, polyimino carbonates, polyurethanes, polyanhydrides, and copolymers and any combinations thereof. Suitable natural biodegradable polymers include collagen, chitin, chitosan, cellulose, polyaminoacids, polysaccharides, and copolymers, derivatives and combinations thereof. The bioresorbable polymer is preferably selected from the group consisting of bioabsorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof.

In addition to the bioresorbable polymer the bioresorbable glass fiber reinforced polymer matrix comprises a bioresorbable reinforcing glass fiber or fiber bundle.

The average fiber diameter of a single reinforcing fiber is in the range of 1-100 micrometers, preferably 5-30 micrometers, more preferably 10-20 micrometers. This may be detected and determined microscopically.

In a preferred example, the bioresorbable reinforcing glass fiber or fiber bundle comprises or is comprised of phosphate or silica-based mineral compound. Most preferably the bioresorbable reinforcing fiber or fiber bundle is a melt derived silica-based bioresorbable glass fiber. In one embodiment the bioresorbable glass is selected from silica, phosphate, boron and magnesium based bioresorbable glasses.

Typically, glass fibers are formed by attenuating streams of a molten glass material from a bushing. A sizing composition, or chemical treatment, may comprise lubricants, coupling agents, film-forming, binders, emulsifiers, surfactants, melt viscosity reducers, compatibilizers, adhesion promoters and anti-static agents, wetting agents, dispersing agents, catalysts, but not limited on those. Sizing's are typically applied to the fibers after they are drawn from the bushing. The sizing composition protects the fibers from inter-filament abrasion and promotes compatibility and adhesion between the glass fibers and the matrix in which the glass fibers are to be used. After the fibers are treated with the sizing composition, they may be dried and formed into a continuous fiber strand package or chopped into chopped strand segments. Glass fibers can then be used in the form of continuous or chopped filaments, strands, roving's, woven fabrics, nonwoven fabrics, meshes, and scrims in polymer matrix.

The bioresorbable glass fiber may comprise or have composition in the following wt % ranges (as a percent over the total weight of the glass fiber composition):

| | |
|---|---|
| $SiO_2$ | 40-90 wt %, |
| $Na_2O$ | 1-30 wt %, |
| $K_2O$ | 0-20 wt %, |
| CaO | 5-30 wt %, |
| MgO | 0-20 wt %, |
| $P_2O_5$ | 0-20 wt %, |
| $B_2O_3$ | 0-20 wt %, |
| $Al_2O_3$ | 0-10 wt %, |
| $CaF_3$ | 0-25 wt %, |
| SrO | 0-10 wt %, and |
| $Li_2O$ | 0-5 wt %. |

In a first example the bioresorbable glass fiber has composition in the following wt % ranges:

| | |
|---|---|
| $SiO_2$ | 50-75 wt %, |
| $Na_2O$ | 5-20 wt %, |
| $K_2O$ | 0-10 wt %, |
| CaO | 5-25 wt %, |
| MgO | 0-10 wt %, |
| $P_2O_5$ | 0.5-5 wt %, |
| $B_2O_3$ | 0-15 wt %, |
| $Al_2O_3$ | 0-5 wt %, and |
| SrO | 0-5 wt %. |

In a second example the melt derived bioabsorbable glass fiber has composition in the following wt % ranges:

| | |
|---|---|
| $SiO_2$ | 60-72 wt %, |
| $Na_2O$ | 10-20 wt %, |
| $K_2O$ | 0.1-10 wt %, |
| CaO | 5-15 wt %, |
| MgO | 1-10 wt %, |
| $P_2O_5$ | 0.5-2 wt %, |
| SrO | 0-3 wt %, and |
| $B_2O_3$ | 0-10 wt %. |

The sum of the ingredients of the compositions sum up to 100%.

Therefore, the present application also discloses a bioresorbable glass fiber and a composition for forming the bioresorbable glass fiber. As used herein, the term "bioresorbable glass fiber" is meant to denote that the glass fiber can be dissolved and/or degraded by the action of water or other natural agents. The bioresorbable fibers may be used as reinforcement for composite parts. The bioresorbable reinforcing glass fiber may be bioactive and/or osteoconductive depending on the glass composition The bioresorbable glass fiber may be used in conjunction with bioresorbable polymers and magnesium or its alloys to form a hybrid composite product that is naturally non-toxic, biocompatible, bioresorbable, biosoluble and biodegradable over a period of time. The bioresorbable fibers have mechanical properties comparative to conventional, non-soluble glass fibers, have a slow to high rate of dissolution in an aqueous medium i.e. low hydrolytic strength and are easily fiberized.

In an advantageous example of the hybrid composite, the bioresorbable glass fiber reinforced polymer matrix comprises a bioresorbable polymer which is preferably selected from the group consisting of bioresorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof; and the bioresorbable reinforcing glass fiber or fiber bundle comprised of a melt derived bioresorbable glass fiber. Preferably the composition of the melt derived bioresorbable glass fiber is as defined above.

In addition to polymer matrix and the bioresorbable reinforcing glass fiber or fiber bundle the bioresorbable glass fiber reinforced polymer matrix may also comprise a bioresorbable sizing in bioresorbable reinforcing glass fiber for improving adhesion between inorganic glass and organic polymer phase, improve processability of the bioresorbable glass fiber reinforced polymer matrix and fiber dispersion in polymer matrix.

Additionally or alternatively the bioresorbable glass fiber reinforced polymer matrix may also comprise one or more reinforcements or filler materials besides of bioresorbable glass fiber, such as ceramic particles (e.g. tricalcium phosphate particles), antimicrobial agents, bioactive agents, active pharmaceutical ingredients, other reinforcing fibers may be comprise other bioresorbable glass composition or glass-like materials, a ceramic, a mineral composition such as hydroxyapatite, tricalcium phosphate, calcium sulfate or calcium phosphate, a cellulosic material, or any other continuous fiber known in the art to increase the mechanical properties of a bioresorbable polymer. The continuous reinforcing fiber may also be a bioresorbable polymer itself.

The embodiments and variants described above in connection with any of the aspects of the present invention apply mutatis mutandis to the other aspects of the invention.

Embodiments of the present invention will now be described in detail in the following examples of the Experimental part. The examples are illustrative but not limiting the compositions, methods, applications and use of the present invention.

EXAMPLES

Example 1

Figure 4:
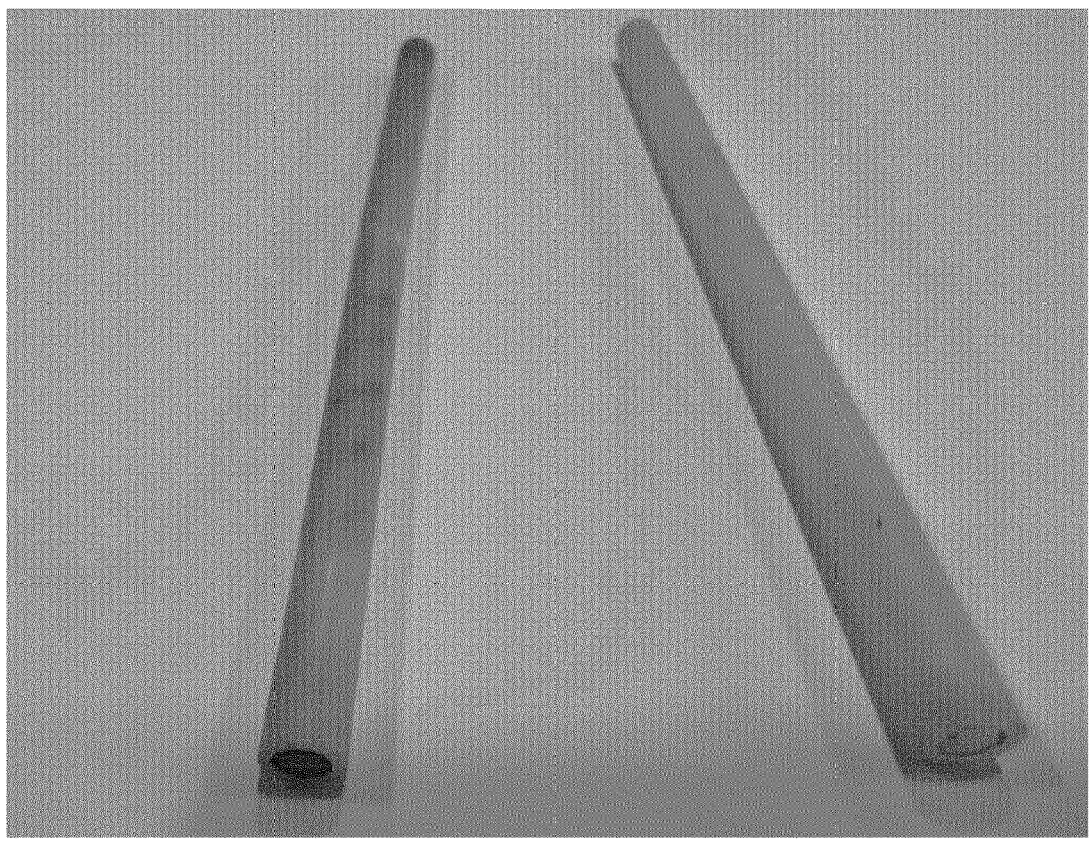
FIG. 4 shows a photo of a manufactured glass fiber polymer composite tube and a hybrid composite product

7 mm diameter round rods of hybrid composite (FIG. 1) were manufactured by machining a magnesium alloy rod (SynerMag 430, Luxfer Mel Technologies) and bioresorbable glass fiber unidirectionally reinforced PLDLA rod (Evolvecomp™ GF40PLD96, Arctic Biomaterials, Bioresorbable glass fiber to PLDLA ratio in weight percent 40:60) with weight percent ratio 50:50 and compressed to form final hybrid composite test sample. More particularly the magnesium alloy rod as a core was inserted into an aperture in a glass fiber polymer composite tube obtained by machining. FIG. 4 shows photos of the machined glass fiber polymer composite tube (left) and the hybrid composite product with the magnesium alloy rod inserted (right).

Example 2

Hybrid composite samples manufactured according to Example 1 were put into three-point-bending test to measure flexural strength and flexural modulus according to ISO 178:2019 (span 16:1, rate 1 mm/min). Mg alloy (SynerMag 430), bioresorbable glass fiber reinforced PLDLA (Evolvecomp™ GF40PLD96) and Bioresorbable self-reinforced SR-PLGLA (Resomer LG 857 S, Evonik) rod as a reference material. The measured flexural strength and flexular modulus are shown in Table 2.

TABLE 2

|  | Flexural strength [MPa] | Flexural modulus [GPa] |
| --- | --- | --- |
| Mg alloy | 395 | 43.6 |
| Evolvecomp ™ GF40PLD96 | 462 | 17.8 |
| SR-PLGLA | 150 | 6.2 |
| Hybrid composite | 390 | 24.1 |

Example 3

Hybrid composite samples manufactured according to example 1 were put into double shear test to measure shear strength according to BS 2782-3 method 340A-B (rate 10 mm/min). Mg alloy (SynerMag 430), bioresorbable glass fiber reinforced PLDLA (Evolvecomp™ GF40PLD96) and Bioresorbable self-reinforced SR-PLGLA (Resomer LG 857 S, Evonik) rod as a reference material. The measured diameter and flexural strength are shown in Table 3.

TABLE 3

|  | Diameter [mm] | Shear strength [N] |
| --- | --- | --- |
| Mg alloy | 7.1 | 5815 |
| Evolvecomp ™ GF40PLD96 | 7.0 | 3988 |
| SR-PLGLA | 6.1 | 1880 |
| SR-PLGLA | 8.1 | 3310 |
| Hybrid composite | 7.0 | 4525 |

Example 4

7 mm diameter round rods of hybrid composite were manufactured by tape winding (FIG. 2) bioresorbable glass fiber unidirectionally reinforced PLDLA tape (Evolvecomp™ GF40PLD96, Arctic Biomaterials) around magnesium alloy rod (MgCaZn where Ca 0.5 wt.-% and Zn 0.5 wt.-%, de Cavis AG) in 45°/45° angle with weight percent ratio 50:50 and compression molded to form final hybrid composite test sample. Mg alloy was chemically coated before tape winding by 3-glycidyloxypropyltriethoxysilane (Dynasylan GLYEO, Evonik) by dip coating mg alloy into 5% ethanol solution (ph 4.5 adjusted by acetic acid) and cured 4 hours at 120° C. Compression molding conditions were 200° C. for 5 minutes with 200 kN pressing force and cooled with a chilled water temperature of 10° C. (a cooling rate of 80 K/min).

Example 5

Hybrid composite samples manufactured according to example 2 were put into three-point-bending test to measure flexural strength and flexural modulus according to ISO 178:2019 (span 16:1, rate 1 mm/min). The measured flexural strength and flexular modulus are shown in Table 4.

TABLE 4

|  | Flexural strength [MPa] | Flexural modulus [GPa] |
| --- | --- | --- |
| Hybrid composite | 379 | 24.1 |

Example 6

Figure 5:
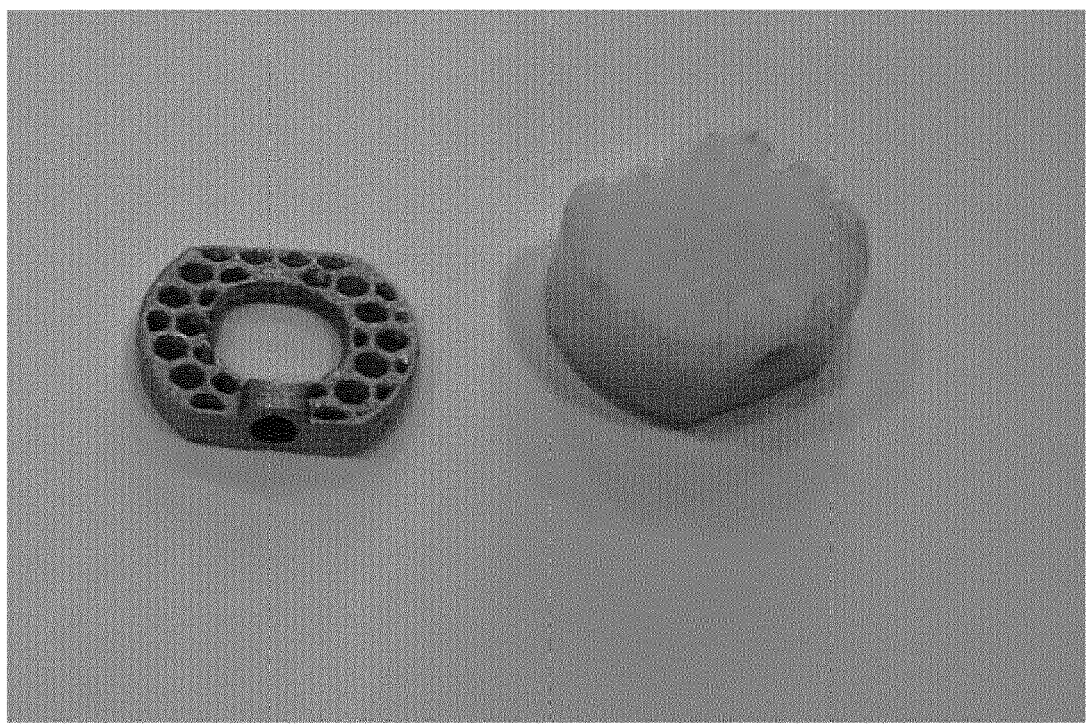
FIG. 5 shows a photo of a magnesium insert of a cage and a manufactured hybrid composite cage containing the magnesium insert and surrounded by wound glass fiber polymer tape

Hybrid composite spinal cage shown in FIG. 5 was manufactured from magnesium alloy core with a cellular structure and from bioresorbable glass fiber reinforced PLDLA (Evolvecomp GF40PLD96). The magnesium alloy core (left) was filament wound with bioresorbable glass fiber reinforced PLDLA tape and then over-molded with bioresorbable glass fiber reinforced PLDLA longitudinal granules in a compression molding machine to obtain the final cage (right). The tape winding provides ultimate radial strength and creep resistance, while the compression molded granules fill the magnesium alloy cavities and provide suitable rough surface texture (on the top).

Figure 6B:
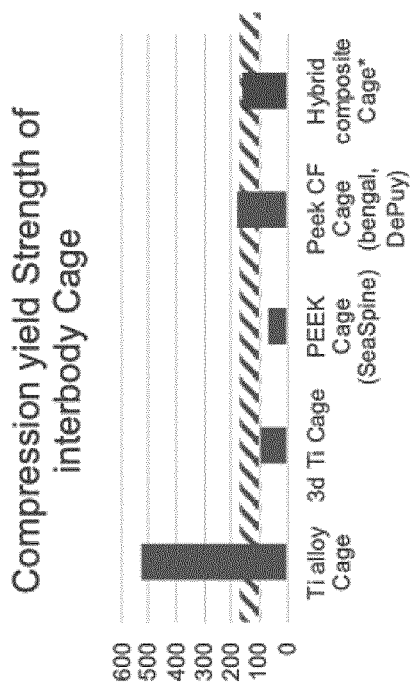
FIGS. 6A and 6B show mechanical properties (elastic modulus and compression yield strength) measured from manufactured hybrid composite cages and compared to literature values of commercially available cage materials and cortical bone
Figure 6A:
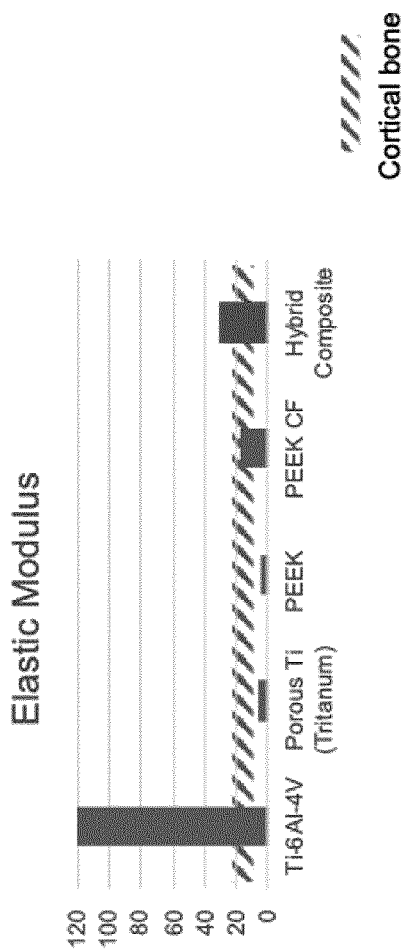

The ratio of the magnesium alloy and bioresorbable glass fiber reinforced PLDLA was 50:50. Mechanical properties (elastic modulus and compression yield strength, FIGS. 6A and 6B) were measured from the manufactured hybrid composite cages and compared to literature values of commercially available cage materials and cortical bone (male, 35 years old) values. The hybrid composite showed isoelastic behavior similar to cortical bone. It can be also seen how the properties of conventionally used titanium materials differ from the properties of the cortical bone.

Example 7

Figure 7A:
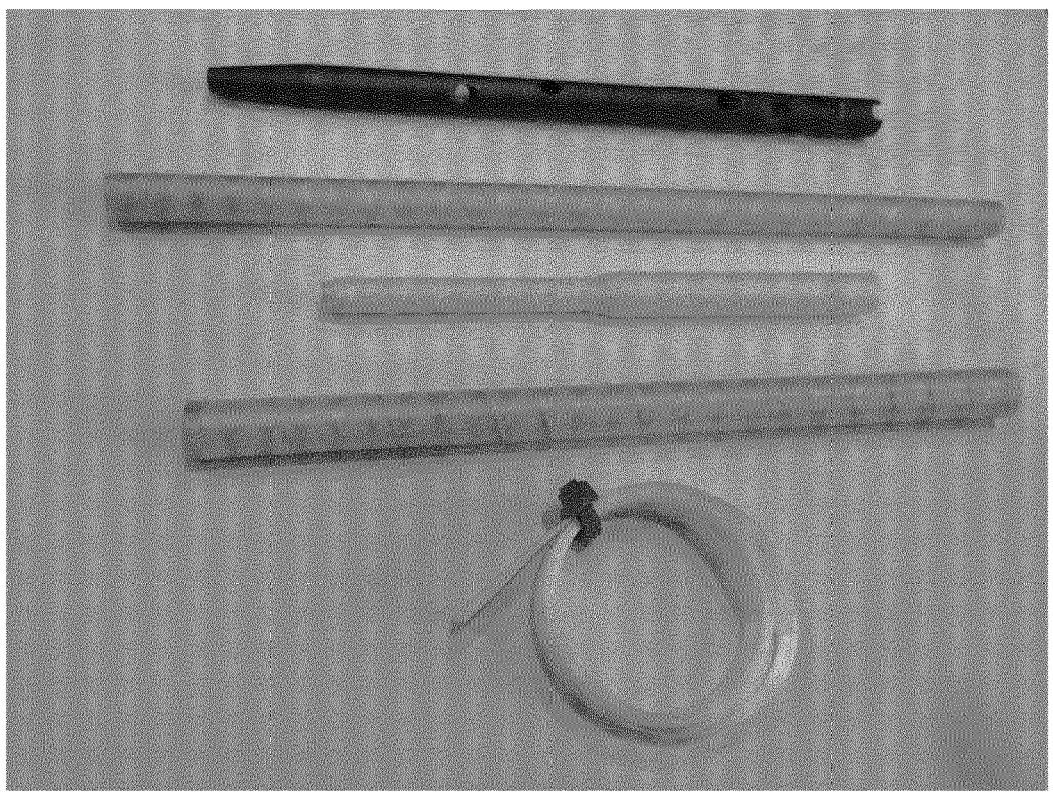
FIGS. 7A and 7B show photos of a magnesium core tube, three hybrid composite products obtained by tape winding, and a coil of glass fiber polymer tape used in the tape winding
Figure 7B:
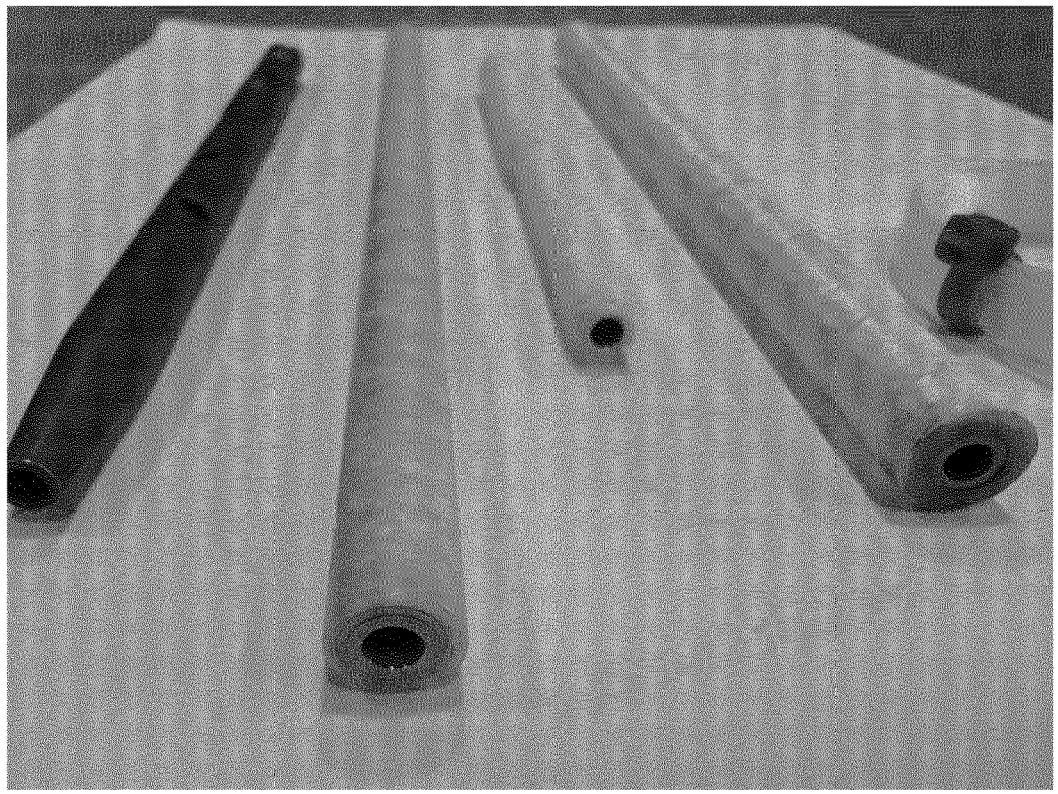

Different hybrid composite products were obtained by tape winding magnesium alloy core tubes with bioresorbable glass fiber unidirectionally reinforced PLDLA tape (Evolvecomp™ GF40PLD96, Arctic Biomaterials), as explained in Example 4. FIGS. 7A and 7B show photos of a magnesium core tube, three hybrid composite products obtained by tape winding, and a roll of glass fiber polymer tape used in the tape winding.

The invention claimed is:

1. A fully biodegradable composite material comprising a bioresorbable self-supporting magnesium or magnesium alloy core in a reinforcing form embedded in bioresorbable glass fiber reinforced polymer matrix, wherein the amount of the magnesium or the magnesium alloy in the composite material is 10-90 weight % of the total weight of the composite material.

2. The composite material of claim 1, wherein the polymer in the polymer matrix comprises one or more of polymers made from, obtained from, or comprising lactide, glycolide, caprolactone, valerolactone, carbonates, dioxanones, 6-valerolactone, ethylene glycol, ethylene oxide, esteramides, γ-hydroxyvalerate, β-hydroxypropionate, alpha-hydroxyacid, hydroxybuterates, polyorthoesters, hydroxy alkanoates, tyrosine carbonates, polyimide carbonates, polyimino carbonates, polyurethanes, polyanhydrides, copolymers, and any combinations thereof.

3. The composite material of claim 2, wherein the polymer in the polymer matrix comprises one or more of polymers made from, obtained from or comprising natural biodegradable polymers including collagen, chitin, chitosan, cellulose, polyaminoacids, polysaccharides, and copolymers, derivatives and combinations thereof, including polymer(s) selected from the group consisting of bioabsorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof.

4. The composite material of claim 3, wherein the bioresorbable reinforcing fiber content is 20 to 80 wt % of the total weight of the bioresorbable glass fiber reinforced polymer matrix.

5. The composite material of claim 1, wherein the magnesium or the magnesium alloy is in a form of a rod, a plate, a tube or fibers.

6. The composite material of claim 1, comprising two or more types of magnesium alloys, each type having different composition, or comprising a second bioresorbable metal besides of primary magnesium or magnesium alloys.

7. The composite material of claim 1, wherein the magnesium or the magnesium alloy is coated, either fully or partially, with one or more of organo-silanes, organo-titanates, organo-zirkonates, functionalized biodegradable polymers with capability to react with surface treated or untreated magnesium or its alloys, aluminum oxide, zinc oxide, metals selected from zinc, gold, silver, copper, and nickel.

8. The composite material of claim 1 comprising two or more types of resorbable and biocompatible glasses or glass fibers, each type having a different composition, resorption rate and/or bioactivity.

9. The composite material of claim 1 comprising free fiber orientation in a one or more successive layers, wherein the layer comprises a bioresorbable polymer matrix and a bioresorbable reinforcing fiber or fiber bundle.

10. The composite material of claim 1, wherein the bioresorbable reinforcing fiber content is 1 to 99 wt % of the total weight of the bioresorbable glass fiber reinforced polymer matrix.

11. The composite material of claim 1, wherein the average fiber diameter of a single reinforcing fiber is in the range of 1-100 micrometers.

12. The composite material of claim 1, wherein the bioresorbable glass comprises

| | |
|---|---|
| $SiO_2$ | 40-90 wt %, |
| $Na_2O$ | 1-30 wt %, |
| $K_2O$ | 0-20 wt %, |
| CaO | 5-30 wt %, |
| MgO | 0-20 wt %, |
| $P_2O_5$ | 0-20 wt %, |
| $B_2O_3$ | 0-20 wt %, |
| $Al_2O_3$ | 0-10 wt %, |
| $CaF_3$ | 0-25 wt %, |
| SrO | 0-10 wt %, and |
| $Li_2O$ | 0-5 wt %. |

13. The composite material of claim 1, wherein the bioresorbable glass is selected from silica, phosphate, boron and magnesium based bioresorbable glasses.

14. The composite material of claim 1 having a flexural strength of 200-1500 MPa measured by ISO 178:2019 or ASTM D790-17.

15. The composite material of claim 1 having a flexural modulus of 20-40 GPa measured by ISO 178:2019 or ASTM D790-17.

16. The composite material of claim 1, wherein the amount of the magnesium or the magnesium alloy in the composite is 20-80 weight %.

17. An orthopedic implant comprising the composite material of claim 1.

18. The composite material of claim 1, obtained by
providing a self-supporting reinforcing form of bioresorbable magnesium or magnesium alloy core,
providing bioresorbable glass fibers,
providing bioresorbable polymer,
combining the materials to form biodegradable composite material comprising bioresorbable magnesium or magnesium alloy in a reinforcing form embedded in bioresorbable glass fiber reinforced polymer matrix.

19. A bioresorbable implant comprising the composite material of claim 1 selected from a screw, a plate, a pin, a tack or a nail for the fixation of bone fractures and/or osteotomies to immobilize the bone fragments for healing; a suture anchor, a tack, a screw, a bolt, a nail, a clamp, a stent and other devices for bone-to-bone, soft tissue-to-bone, soft tissue-into-bone and soft tissue-to-soft tissue fixation; devices used for supporting tissue or bone healing or regeneration; or cervical wedges and lumbar cages and plates and screws for vertebral fusion and other operations in spinal surgery.

20. The bioresorbable implant of claim 19, wherein the bioresorbable implant comprises or is an intramedullary nail.

21. The bioresorbable implant of claim 19, wherein the bioresorbable implant comprises or is a scaffold or a cage.

22. A medical treatment method comprising
recognizing a subject in need of treatment or therapy,
providing the bioresorbable implant of claim 19,
inserting the bioresorbable implant into the subject.

* * * * *